United States Patent [19]
Matzke et al.

[11] Patent Number: 6,096,656
[45] Date of Patent: Aug. 1, 2000

[54] FORMATION OF MICROCHANNELS FROM LOW-TEMPERATURE PLASMA-DEPOSITED SILICON OXYNITRIDE

[75] Inventors: Carolyn M. Matzke, Los Lunas; Carol I. H. Ashby, Edgewood; Monica M. Bridges; Ronald P. Manginell, both of Albuquerque, all of N. Mex.

[73] Assignee: Sandia Corporation, Albuquerque, N. Mex.

[21] Appl. No.: 09/339,715

[22] Filed: Jun. 24, 1999

[51] Int. Cl.$^7$ ................................................. H01L 21/00
[52] U.S. Cl. ..................... 438/702; 438/694; 438/698; 438/700; 205/122; 216/2; 156/643.1
[58] Field of Search ............................. 205/122; 216/2; 156/643.1; 438/694, 697, 700, 702

[56] References Cited

U.S. PATENT DOCUMENTS

| | | | |
|---|---|---|---|
| 5,252,294 | 10/1993 | Kroy | 422/102 |
| 5,501,893 | 3/1996 | Laermer | 428/161 |
| 5,569,355 | 10/1996 | Then et al. | 156/643.1 |
| 5,585,069 | 12/1996 | Zanzucchi | 422/100 |
| 5,632,876 | 5/1997 | Zanzucchi | 204/600 |
| 5,660,728 | 8/1997 | Saaski | 210/251 |
| 5,681,484 | 10/1997 | Zanzucchi | 216/2 |
| 5,729,244 | 3/1998 | Lockwood | 345/74 |
| 5,755,408 | 5/1998 | Schmidt | 244/204 |
| 5,783,452 | 7/1998 | Jons | 436/183 |
| 5,801,442 | 9/1998 | Hamilton | 257/714 |
| 5,858,193 | 1/1999 | Zanzucchi | 204/601 |
| 5,863,708 | 1/1999 | Zanzucchi | 430/320 |
| 5,871,158 | 2/1999 | Frazier | 239/548 |
| 5,876,582 | 3/1999 | Frazier | 205/122 |
| 5,876,675 | 3/1999 | Kennedy | 422/99 |
| 5,897,097 | 4/1999 | Biegelsen | 251/129.01 |
| 5,909,280 | 6/1999 | Zavracky | 356/352 |

OTHER PUBLICATIONS

C.M. Matzke, D.W. Arnold, C.I.H. Ashby, S.H. Kravitz, M.E. Warren and G.C. Bailey, "Quartz Channel Fabrication for Electrokinetically Driven Separations," *Proceedings of the SPIE Conference on Microfluidic Devices and Systems,* SPIE vol. 3515, pp. 164–171, Sep. 1998.

C.M. Matzke, R.J. Kottenstette, S.A. Casalnuovo, G.C. Frye–Mason, M.L. Hudson, D.Y. Sasaki, R.P. Manginell, and C.C. Wong, "Microfabricated Silicon Gas Chromatographic Micro–Channels: Fabrication and Performance," *Proceedings of the SPIE Conference on Micromachining and Microfabrication Process Technology IV,* SPIE vol. 3511, pp. 262–268, Sep. 1998.

S. Sitbon, M.C. Hugon, B. Agius, F. Abel, J.L. Courant and M. Puech, Low Temperature Deposition of Silicon Nitride Films by Distributed Electron Cyclotron Resonance Plasma–Enhanced Chemical Vapor Deposition, *Journal of Vacuum Science and Technology A,* vol. 13, pp. 2900–2907, Nov./Dec. 1995.

*Primary Examiner*—Charles Bowers
*Assistant Examiner*—Lisa Kilday
*Attorney, Agent, or Firm*—John P. Hohimer

[57] ABSTRACT

A process for forming one or more fluid microchannels on a substrate is disclosed that is compatible with the formation of integrated circuitry on the substrate. The microchannels can be formed below an upper surface of the substrate, above the upper surface, or both. The microchannels are formed by depositing a covering layer of silicon oxynitride over a mold formed of a sacrificial material such as photoresist which can later be removed. The silicon oxynitride is deposited at a low temperature ($\leq 100°$ C.) and preferably near room temperature using a high-density plasma (e.g. an electron-cyclotron resonance plasma or an inductively-coupled plasma). In some embodiments of the present invention, the microchannels can be completely lined with silicon oxynitride to present a uniform material composition to a fluid therein. The present invention has applications for forming microchannels for use in chromatography and electrophoresis. Additionally, the microchannels can be used for electrokinetic pumping, or for localized or global substrate cooling.

40 Claims, 16 Drawing Sheets

Section 1 - 1

Section 2 - 2

6,096,656

FORMATION OF MICROCHANNELS FROM LOW-TEMPERATURE PLASMA-DEPOSITED SILICON OXYNITRIDE

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates generally to fluidic channels formed on or within a substrate, and specifically to a process for forming fluidic microchannels from one or more layers of silicon oxynitride deposited at a low temperature using a high-density plasma deposition process.

BACKGROUND OF THE INVENTION

The formation of one or more microchannels on or within a substrate is useful for many different types of microfluidic applications, including micro analysis systems, micromechanical actuators, localized or global substrate cooling, and ink-jet printing. Micro analysis systems which utilize microminiature fluid channels include liquid and gas chromatography, electrophoresis, free-flow fractionation, and polmerase chain reaction.

Conventional methods for forming microchannels generally rely on the fabrication of the microchannels in a substrate, and then adhering or wafer bonding a cover plate over the substrate seal the microchannels (see e.g. U.S. Pat. No. 5,575,929 to Yu et al). Such conventional methods for forming microchannels can be problematic due to particulate contamination on the substrate or adhesive contamination in the microchannels. Furthermore, these conventional methods can require that the substrate be flat without any local or global warp. Finally, these conventional methods are generally not compatible with the formation of an integrated circuit on the substrate.

For many applications of microchannels, it is desirable to be able to form electronic circuitry on the same substrate as the microchannels. Such circuitry can be used to produce a flow of a particular fluid by electrokinetic pumping which can be used for separating specific components of the fluid (e.g. chromatographic or electrophoretic separation). Additionally, the provision of electronic circuitry on the substrate can be used for resistively heating the fluid, and/or for detection of specific components in the fluid for chemical analysis. Finally, electronic circuitry on the substrate can be used for signal processing, thereby forming a smart sensor.

Prior methods for forming microchannels on a substrate that are compatible with integrated circuit processing include the use of electroplated metals (see e.g. U.S. Pat. Nos. 5,871,158 and 5,876,582 to Frazier) and the deposition of various materials (e.g. silicon-carbon materials) by plasma enhanced chemical vapor deposition (see U.S. Pat. No. 5,783,452 to Jons et al).

An advantage of the present invention is that a process is disclosed whereby one or more hollow microchannels can be formed on or below a surface of a substrate, or both.

A further advantage of the present invention is that the microchannels can be fabricated using common clean-room techniques and equipment for compatibility with integrated circuit processing.

Yet another advantage of the present invention is that the microchannels can be formed at a low temperature less than 100° C. and preferably near room temperature to eliminate detrimental effects to some materials (e.g. photoresist) used in forming the microchannels. The use of low temperature processes for forming the microchannels is also advantageous for compatibility with low-melting-point substrates (e.g. polymer substrates) or for certain metallizations (e.g. aluminum) on the substrate prior to forming the microchannels.

Yet another advantage of the present invention is that the microchannels can be formed completely lined with a silicon oxynitride material to present a uniform composition surface for fluid flow, thereby eliminating possible detrimental effects due to contact of the fluid with surfaces of different compositions, or with the substrate.

Still another advantage of the present invention is that the use of silicon oxynitride to form the microchannels produces microchannels which are electrically insulating for operation at high voltages as required for electrokinetic separations.

These and other advantages of the present invention will become evident to those skilled in the art.

SUMMARY OF THE INVENTION

The present invention relates to a method for forming one or more fluid microchannels in a substrate, comprising steps for forming a trench below an upper surface of the substrate at the location of each microchannel to be formed, filling each trench with a sacrificial material; forming at least one silicon oxynitride layer covering each trench; and removing the sacrificial material from each trench to form the completed microchannel.

In some preferred embodiments of the present invention, each trench is formed by etching the substrate; whereas in other embodiments of the present invention, the trench can be formed by any method known to the art, including mechanical abrasion, molding, ion milling or laser ablation. Many different types of substrates are suitable for practice of the present invention, including semiconductors (e.g. silicon, germanium, gallium arsenide), glasses, ceramics, polymers (i.e. plastics), resins, metals (including metal alloys), ferroelectrics, crystalline quartz and fused silica. The trench formed in the substrate can be of arbitrary cross-section shape and length, with sidewalls of the trench being curved, straight (i.e. substantially perpendicular to the upper surface of the substrate) or angled. Additionally, the trench can be straight, curved, or serpentine shaped. Finally, the trench can include a plurality of shaped columns aligned substantially perpendicular to the upper surface of the substrate.

The step for filling the trench with the sacrificial material preferably comprises filling the trench with a photoresist; and the step for removing the sacrificial material preferably comprises removing the photoresist from the trench by dissolution using a solvent (e.g. acetone). To fill the trench with the photoresist, the photoresist is initially spun on over the surface of the substrate and in the trench, and then a portion of the photoresist is photolithographically exposed and developed to remove a portion of the photoresist outside the trench. Any photoresist residue remaining on the surface of the substrate can be removed with a cleaning step which preferably comprises exposing the substrate to an oxygen plasma.

Formation of the silicon oxynitride layer covering the trench is preferably performed by a high-density plasma deposition process which is carried on at a low temperature of $\leq 100°$ C., and preferably near room temperature (e.g.

20–30° C.). Many different high-density plasma deposition processes are suitable for practice of the present invention including electron-cyclotron resonance (ECR) plasma deposition and inductively-coupled plasma (ICP) deposition, but specifically excluding plasma-enhanced chemical vapor deposition (PECVD) which is a low-density plasma deposition process that proceeds at a temperature sufficiently high to lead to a polymerization of the photoresist thereby making its removal difficult. A high-density plasma deposition process is defined herein as a process carried out in a plasma containing at least $10^{11}$ electrons/cm$^3$ and generally up to about $5\times10^{13}$ electrons/cm$^3$. Additionally, a high-density plasma deposition process can be defined as a plasma process which provides a positive ion flux to the surface of the substrate in the range of 1–50 mA/cm$^2$.

The silicon oxynitride layer can comprise a partially hydrogenated silicon oxynitride having a composition $Si_wO_xN_yH_z$, with w being in the range of 25–65 atomic percent (at. %) silicon, x being in the range of 5–40 at. % oxygen, y being in the range of 10–40 at. % nitrogen, and z being in the range of 0–25 at. % hydrogen. After removing the sacrificial material from the trench, the silicon oxynitride layer(s) can optionally be densified by a thermal annealing step, thereby strengthening the microchannel(s) and lowering the hydrogen content in the silicon oxynitride composition.

Removal of the sacrificial material from the trench can be accomplished, for example, by forming one or more openings through the silicon oxynitride layer to expose the sacrificial material which is preferably a photoresist. The photoresist can then be removed by dissolution by a solvent (e.g. acetone) with or without agitation or heating. Once the photoresist is removed, the openings through the silicon oxynitride layer can be sealed, for example, with one or more additional depositions of silicon oxynitride. Optionally, one or more encapsulating layers can be deposited over the silicon oxynitride layer(s) to further strengthen the microchannel(s) for protection, or to withstand a high internal fluid pressure.

In some embodiments of the present invention (e.g. for chromatography or electrophoresis) it is desirable that the microchannel present a uniform composition to a fluid of interest for efficient operation. This can be accomplished by lining the trench with an underlayer of silicon oxynitride prior to filling the trench with the sacrificial material. The underlayer can be formed by depositing 0.05–3 microns of silicon oxynitride over the substrate and in the trench using the high-density plasma deposition process.

The present invention further relates to a method for forming one or more fluid microchannels on a substrate by depositing a sacrificial material over an upper surface of the substrate and patterning the sacrificial material to form an elongate-shaped mold to define the microchannel being formed over the substrate, depositing at least one covering layer of silicon oxynitride over the patterned sacrificial material, and providing at least one opening for exposing the sacrificial material, and removing the sacrificial material through the opening. The same types of substrates described previously can be used to form this type of microchannel.

The sacrificial material is preferably a photoresist which is spun on over the upper surface of the substrate and patterned to form the elongate-shaped mold, with the remaining photoresist removed, and with any photoresist residue removed by a cleaning step based on exposure of the upper surface of the substrate to an oxygen plasma. The patterned photoresist can optionally be heated to a temperature sufficient to cause the photoresist to flow, thereby producing a curved cross-section shape for the mold. As described previously, the photoresist can be removed by solvent dissolution (e.g. with acetone).

The step for depositing the covering layer is preferably based on deposition of silicon oxynitride by a high-density plasma deposition process (e.g. an ECR or ICP deposition process) which proceeds at a low substrate temperature of $\leq 100°$ C., and preferably near room temperature. After removal of the sacrificial material, the covering layer can optionally be annealed to increase its density and mechanical strength.

In some embodiments of the present invention, the upper surface of the substrate can be lined with an underlayer of silicon oxynitride prior to deposition of the sacrificial material, thereby permitting the fabrication of a microchannel which presents a uniform material composition to a fluid therein. When an underlayer is used, an exposed portion of the underlayer can be treated prior to deposition of the covering layer to improve adhesion of the covering layer to the exposed portion of the underlayer.

In other embodiments of the present invention, one or more fluid microchannels can be formed which lie partially below the upper surface of the substrate and partially above the upper surface. This can be done by combining the teachings of the two methods described previously to form a trench in the substrate prior to depositing the sacrificial material to a thickness sufficient to extend upward above the surface of the substrate a predetermined distance. Once the sacrificial material (e.g. photoresist) is patterned, the resultant elongate-shaped mold will fill the trench and extend upward beyond the surface of the substrate. The mold can then be covered by depositing a covering layer (e.g. silicon oxynitride) to form the microchannel. The microchannel is completed by removing the sacrificial material (e.g. through at least one opening in the covering layer, or through at least one via-hole through the substrate that connects with the microchannel, or through one or more ends of the microchannel).

When photoresist is used as the sacrificial material, the patterned photoresist can optionally be heated and flowed to generate a curved cross-section shape for the mold. And if the trench is formed with curved sidewalls, the result can be formation of a microchannel having, for example, a circular or elliptical cross-section shape. As described previously, the trench can optionally be lined with an underlayer (e.g. silicon oxynitride) prior to deposition of the sacrificial material. Once the microchannel is formed and the sacrificial material removed, an encapsulating layer can be deposited over the covering layer, if need, to seal openings through the covering layer and/or to provide an increased mechanical strength for the microchannel.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1A:
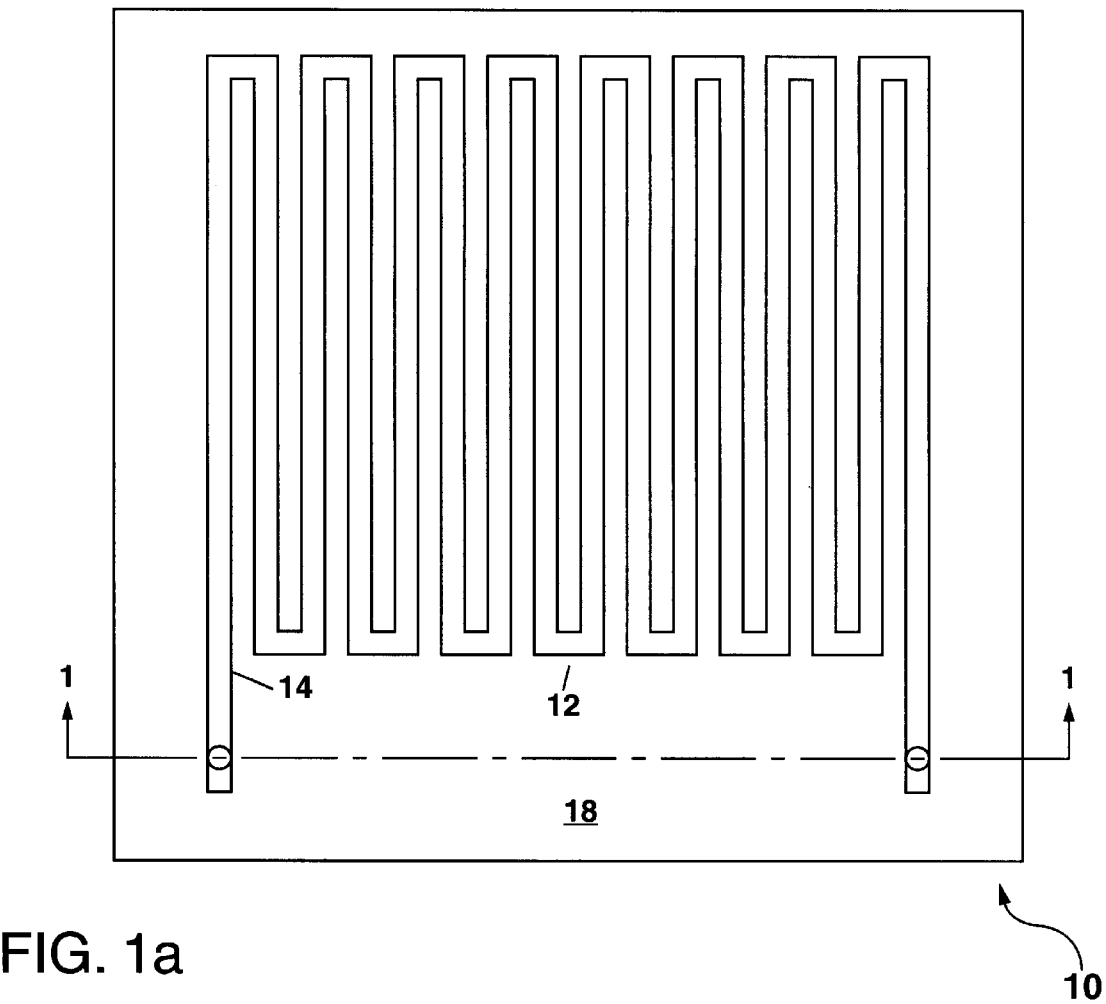
FIG. 1a shows a schematic plan view of an example of a microchannel device having at least one fluid microchannel formed on a substrate according to the present invention.

Referring to FIG. 1a, there is shown schematically in plan view an example of a microchannel device 10 that comprises a fluid microchannel 12 which can be formed according to the present invention. The microchannel 12 comprises a trench 14 formed below an upper surface 16 of a substrate 18, with the trench 14 being covered by at least one deposited silicon oxynitride layer 20. For clarity, the silicon oxynitride layer 20 has been omitted from FIG. 1a, but is shown in the cross-section view of FIG. 1b. As defined herein, the term "microchannel" refers to a hollow fluid duct having a width that is generally in the range from about 5 to 500 microns ($\mu$m), and a height that is generally in the same range as the width. The term "fluid" is intended to include both liquids and gases.

Figure 1B:
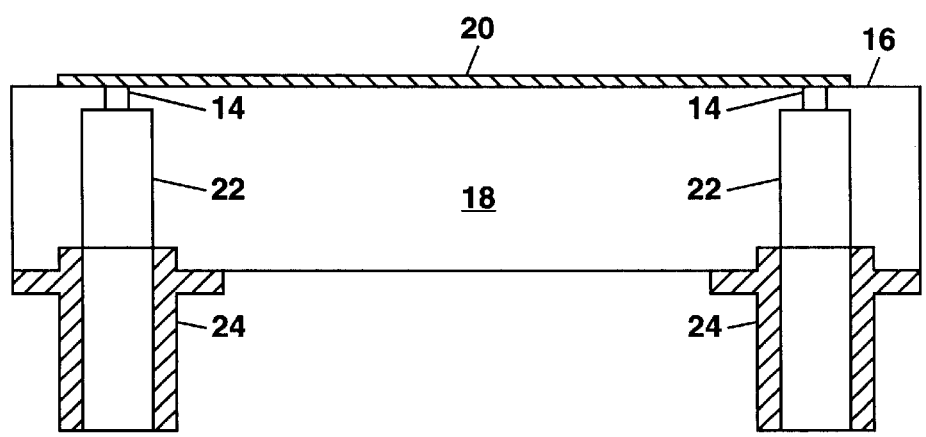
FIG. 1b shows a schematic cross-section view along the lines 1—1 in FIG. 1a to illustrate how external fluid connections can be made through the substrate to the microchannel formed therein.

The microchannel 12 in the example of FIG. 1a has a serpentine shape to save space on the substrate 18 (e.g. for forming a compact gas or liquid chromatograph). External fluid connections (e.g. a sample injection port and an output port) can be provided to either end of the microchannel 12 as shown in FIG. 1b by forming via holes 22 through the lower surface of the substrate 18 to the microchannel 12 and attaching macrotubing 24 (e.g. capillary tubing) to the substrate 18. For mechanical stability, the tubing 24 can be initially epoxied or otherwise attached to small pieces of glass having machined thru-holes to accept the tubing 24; and then the reinforced tubing 24 can be attached to the lower surface of the substrate 18 at the via holes 22 with additional epoxy or other adhesive, or by anodic bonding. Further mechanical stabilization of the completed microchannel device 10 can be provided, if needed, by applying a strengthening material (e.g. a two-part elastomer, an epoxy, a commercial potting compound, a polyimide, or a spin-on glass) to one or both surfaces of the substrate 18.

In the example of FIGS. 1a and 1b, the substrate 18 can comprise either a crystalline or a non-crystalline material. In particular, crystalline materials that can be used for the substrate 18 include semiconductors (e.g. silicon, germanium, gallium arsenide), crystalline quartz, and ferroelectrics (e.g. barium titanite). Non-crystalline materials that can be used as the substrate 18 can include glasses, polymers (i.e. plastics), ceramics (including ferroelectric ceramics), metals (including metal alloys), and fused silica.

Figure 2A:
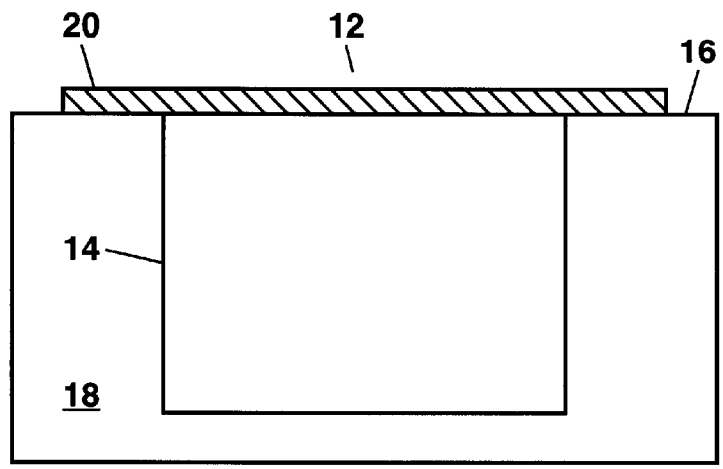
FIGS. 2a and 2b show schematic cross-section views of two examples of fluid microchannels that can be formed below the upper surface of the substrate according to the present invention.

Examples of microchannels 12 that can be formed extending below the surface 16 of the substrate 18 (i.e. sub-surface microchannels 12) according to the present invention are shown schematically in the enlarged cross-section views in FIGS. 2a and 2b. FIG. 2a shows a microchannel 12 comprising a trench 14 having a generally rectangular cross-section shape with a pair of sidewalls aligned substantially perpendicularly to the upper surface 16 of the substrate 18; whereas FIG. 2b shows a microchannel 12 formed in a trench 14 having curved sidewalls.

The exact shape for the trench 14 will depend upon the process selected to form the trench 14, and upon the particular use for which the microchannel 12 is designed. A rectangular trench 14 for the microchannel 12 can be formed, for example, by anisotropic etching (e.g. using an anisotropic wet etchant, or an anisotropic dry etching process such as reactive ion etching), or by ion milling; whereas a trench 14 having curved sidewalls can be formed, for example, by isotropic etching, molding or laser ablation. Other cross-section shapes for the trench 14 are also possible. As an example, a trench 14 with angled sidewalls can be formed by anisotropic wet etching which stops at particular crystalline planes (e.g. {111} planes in a (100) silicon substrate 18 etched by an anisotropic wet etchant such as potassium hydroxide, tetramethyl ammonium hydroxide or ethylenediamine pyrocatechol).

Figure 2B:
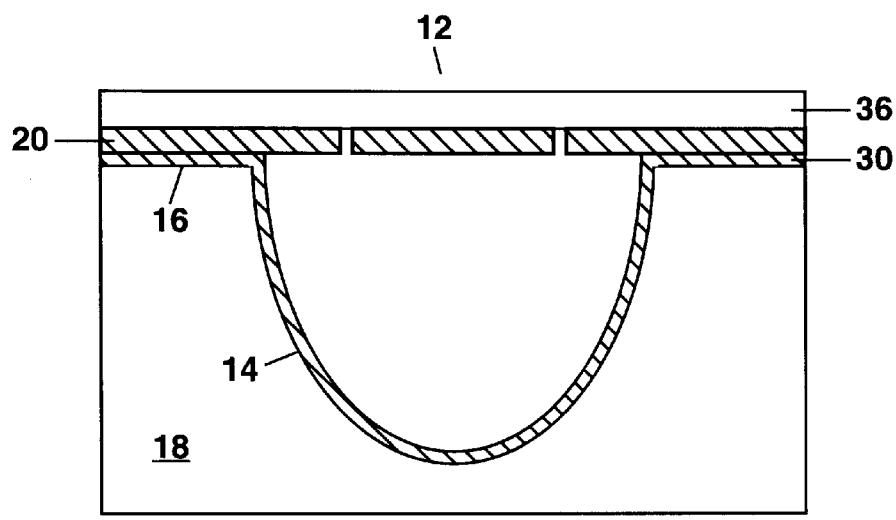

In forming one or more microchannels 12 in a substrate 18 according to the present invention a series of process steps can be used as described hereinafter with reference to FIGS. 3a–3i for the case of a curved microchannel 12 as shown in FIG. 2b. Many of these process steps are also applicable to form the rectangular microchannel 12 of FIG. 2a.

A number of individual process steps are required to form the microchannel 12 of the present invention. Only the relevant process steps for the present invention will be described herein in detail since those skilled in the art understand other conventional semiconductor integrated circuit (IC) processing steps such as photolithography, masking, etching, mask stripping, and cleaning.

Figure 3A:
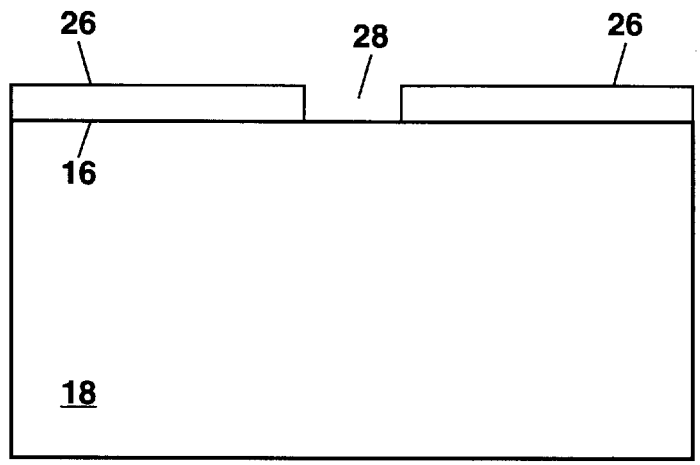
FIGS. 3a–3i illustrate a series of process steps that can be used to form the microchannel of FIG. 2b.

In FIG. 3a, a photoresist or metal mask 26 is formed over the substrate 18 with a slot 28 centered about a predetermined path of the microchannel 12 to be formed in the substrate 18. The size of the slot 28 will, in general, depend upon the size of the microchannel 12 to be formed (i.e. its width and depth). A narrow slot 28 is particularly useful to form a semi-circular microchannel 12 (see U.S. Pat. No. 5,575,929 to Yu et al). As the width of the slot 28 is increased, the width of the isotropically etched microchannel 12 will increase compared to its depth. The present invention can be used to form curved microchannels 12 as shown in FIG. 2b having a width that is generally in the range of about 2–500 μm and preferably about 5–100 μm, and with a depth that is up to about one-half the width.

Figure 3B:
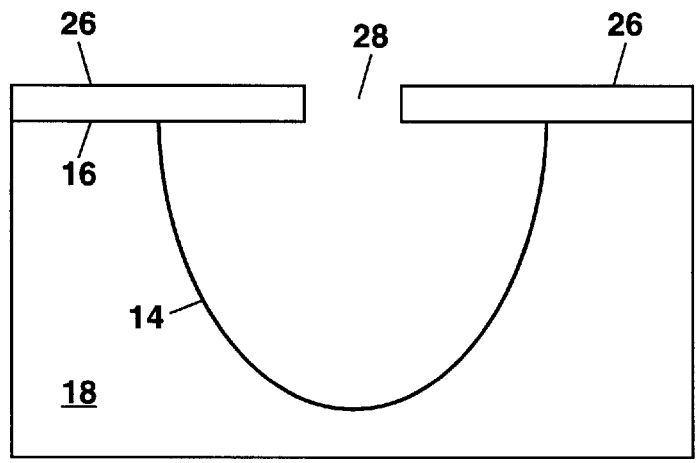

In FIG. 3b, the masked substrate 18 is exposed to an isotropic wet etchant which removes material from the substrate 18 through non-preferential downward and lateral etching, thereby forming a curved trench 14 having a cross-section shape as determined by the shape of the slot 28. Isotropic wet etchants are well known in the art for the various materials which can be used for the substrate 18. For example, an acid mixture containing hydrofluoric acid (HF) and nitric acid ($HNO_3$) and either acetic acid ($CH_3COOH$) or water can be used to isotropically etch a silicon substrate 18. As another example, an HF-based etchant (e.g. a buffered oxide etch) can be used to isotropically etch a glass or fused silica substrate 18.

The present invention is not limited to forming the microchannel 12 by etching. In certain instances it can be preferable to form the microchannel 12 by other methods such as mechanical abrasion, molding (e.g. injection molding, stamping or embossing with or without heating), ion milling or laser ablation depending upon the composition of the substrate and the dimensions and dimensional tolerance required for the microchannel 12. In such cases, the masking step of FIG. 3a can be omitted; and the curved trench 14 can be formed directly by one of the above processes. In the case of a plastic substrate 18, solvent dissolution of the plastic through a patterned mask can also be used to form the trench 14.

Figure 3C:
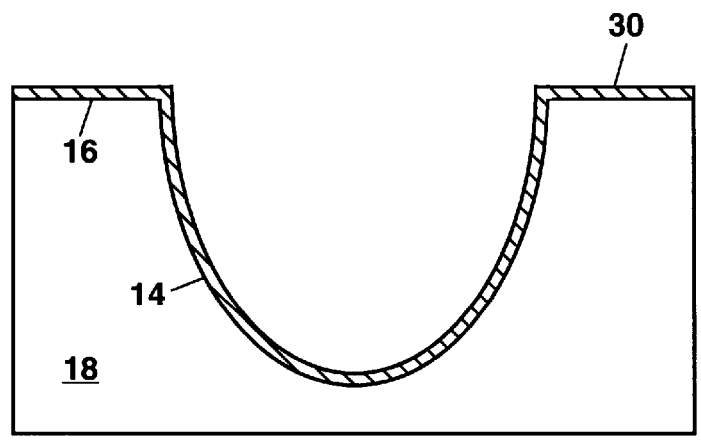

In FIG. 3c, the curved trench 14 can optionally be lined with an underlayer 30 of silicon oxynitride which can be advantageous for certain applications such as chromatography or electrophoresis. This can be done by depositing a 0.05- to 3-μm-thick layer of silicon oxynitride over the substrate 18 and in the curved trench 14 using a high-density plasma deposition process as described hereinafter.

A high-density plasma deposition process is to be distinguished from conventional capacitively-coupled radio-frequency (rf) low-density plasma systems which generally operate with electron densities in the range of $5 \times 10^8$–$5 \times 10^{10}$ cm$^{-3}$, with a positive ion flux of about 0.1–1 mA/cm$^2$. Additional input energy is generally required in a conventional rf low-density plasma; and this additional energy can be provided by heating the substrate to a temperature of about 150° C. or more. Plasma-enhanced chemical vapor deposition (PECVD) is an example of a conventional rf low-density plasma deposition system which is not suited for use in practicing the present invention.

A high-density plasma source operates at a lower pressure and lower ion energy than a conventional rf low-density plasma source, with the high-density plasma source further having a higher electron, ion and neutral radical density (i.e. an electron density of $10^{11}$–$5 \times 10^{13}$ electrons/cm$^3$ and a positive ion flux of 1–50 mA/cm$^2$). In a high-density plasma source, the plasma generation and substrate biasing are independent or semi-independent. Since source gases are more highly dissociated in a high-density plasma, little or no substrate heating is necessary so that deposition can be carried on at a low temperature of about 100° C. or lower, and preferably at or near room temperature. This allows the use of photoresist as the sacrificial material 32, and simplifies removal of the photoresist by solvent dissolution. At temperatures greater than 100° C. for time periods of several minutes or more, there is the possibility for polymerization of the photoresist 32 which can make its removal difficult and possibly result in damage to the microchannel 12.

Examples of high-density plasma deposition systems which can be used to deposit the silicon oxynitride underlayer 30 in FIG. 3c and other silicon oxynitride layers to be described hereinafter include electron-cyclotron resonance (ECR) plasma deposition systems and inductively-coupled plasma (ICP) deposition systems. Other types of high-density plasmas systems that are also suitable for deposition of the silicon oxynitride include helicon plasma systems, multipolar plasma bucket systems, magnetron capacitively-coupled plasma systems and hollow-cathode capacitively-coupled plasma systems.

An ECR plasma deposition system uses microwaves to generate a high-density plasma from supplied source gases, and a magnetic field to keep electrons circulating in the plasma to produce a high electron density and to control beam collimation. No substrate heating is necessary for the ECR plasma deposition system; and a low substrate bias voltage of 0–100 volts. Bias voltages in the low end of the above range (e.g. about 5 volts) are to be preferred to limit etch-back of the deposited silicon oxynitride. Inductively-coupled plasma deposition systems are also referred to as transformer-coupled plasma (TCP) systems or as rf induction (RFI) systems.

To form the silicon oxynitride underlayer 30 with an ECR plasma deposition system, the ECR system can be operated at a microwave power level of generally 80–400 W, and preferably at either 125 or 385 W, with the microwave frequency generally being 2.45 GHz. Source gases which can be used to form the silicon oxynitride layer include silane ($SiH_4$) and one or more of a nitrogen source gas such as nitrogen ($N_2$), nitrous oxide ($N_2O$), or the combination of oxygen ($O_2$) and $N_2$. Argon (Ar) can additionally be added to the plasma.

The ECR high-density plasma can be operated at a pressure of typically 15–30 mTorr, and preferably about 20 mTorr. Flow rates for the source gases can be in the range of 5–50 standard-cubic-centimeters-per-minute (sccm) silane, 5–50 sccm of the nitrogen source gas (i.e. $N_2$, $N_2O$, or $N_2+O_2$), and 0–20 sccm argon. Preferred flow rates are 20 sccm silane, 30 sccm of the nitrogen source, and 4 sccm argon. A 5 volt bias is preferably provided to the substrate 18 with no substrate heating. The silicon oxynitride underlayer 30 can be deposited in the ECR plasma at a rate of 5–150 nanometers/minute, with the silicon oxynitride having a refractive index n=2.0 at a deposition rate of 20 nanometers/minute.

Under the preferred conditions above, a Rutherford backscattering measurement indicated a composition of the ECR-deposited silicon oxynitride as being 40 at. % silicon, 36 at. % nitrogen, 12 at. % oxygen and 12 at. % hydrogen. In general, the silicon oxynitride deposited according to the present invention can comprise a partially hydrogenated silicon oxynitride having a composition $Si_wO_xN_yH_z$, with w being in the range 25–65 at. % silicon, x being in the range 5–40 at. % oxygen, y being in the range 10–40 at. % nitrogen, and z being in the range 0–25 at. % hydrogen. The exact composition of the silicon oxynitride will depend upon the operating parameters of the high-density plasma deposition system, and on whether or not an annealing step is provided to densify the silicon oxynitride thereby lowering its hydrogen content. In forming the silicon oxynitride underlayer 30 with an ICP plasma source, the same source gases can be used and the flow rates and plasma parameters can be adjusted to provide a composition for the silicon oxynitride within the above range as determined from Rutherford backscattering measurements and/or index of refraction measurements.

Figure 3D:
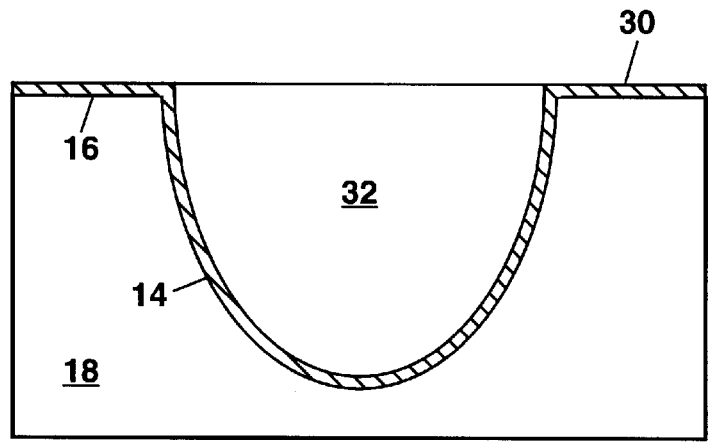

In FIG. 3d, the trench 14 can be filled in with one or more layers of a sacrificial material 32. The term "sacrificial material" as used herein refers to a removable molding material which can be used to define inside dimensions of the microchannel 12 and later removed to leave a hollow microchannel 12 for fluid flow. The sacrificial material 32 preferably comprises photoresist (e.g. a positive tone thick photoresist) or photodefinable polymer (e.g. a photodefinable polyimide) which can be spun on over the substrate 18 in one or more layers to fill the curved trench 14. A short spin time can be used to minimize flow of the photoresist or photodefinable polymer out of the curved trench 14. Additionally, multiple spins and exposures may be needed to fill the trench 14 since each spun-on layer of photoresist is typically only up to 7–9 $\mu$m thick.

Photolithographic patterning and developing can be used to remove substantially all of the photoresist outside the trench 14 as shown in FIG. 3d. In some instances, the photoresist can extend upward beyond the upper surface 16 of the substrate. An oxygen plasma cleansing step (also termed herein a "de-scum" step) can be used to remove any photoresist residue overlying the silicon oxynitride underlayer 30 outside the trench 14, thereby improving the adhesion of a subsequently deposited silicon oxynitride layer 20 (i.e. a covering layer) which is used to complete formation of the curved microchannel 12.

Figure 3E:
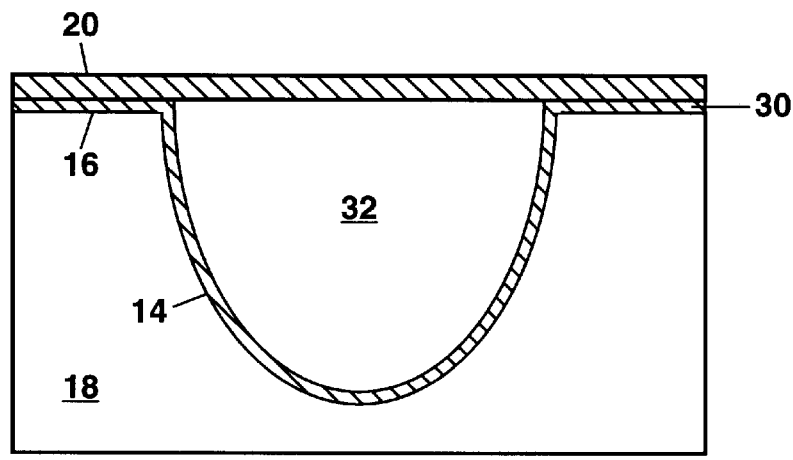

In FIG. 3e, the silicon oxynitride covering layer 20 can be deposited using the same high-density plasma used previously for forming the underlayer 30, except that the covering layer 20 is generally deposited to a greater layer thickness (e.g. about 0.5–10 $\mu$m, and preferably about 2 $\mu$m). During deposition of the silicon oxynitride covering layer 20, it is important to keep the substrate temperature below about 90–100° C. to prevent polymerization of the photoresist 32 in the curved trench 14 which can make the photoresist 32 difficult to remove later. Preferably, the substrate 18 is maintained at or near room temperature (e.g. 20–30° C.) during deposition of the covering layer 20.

Figure 3F:
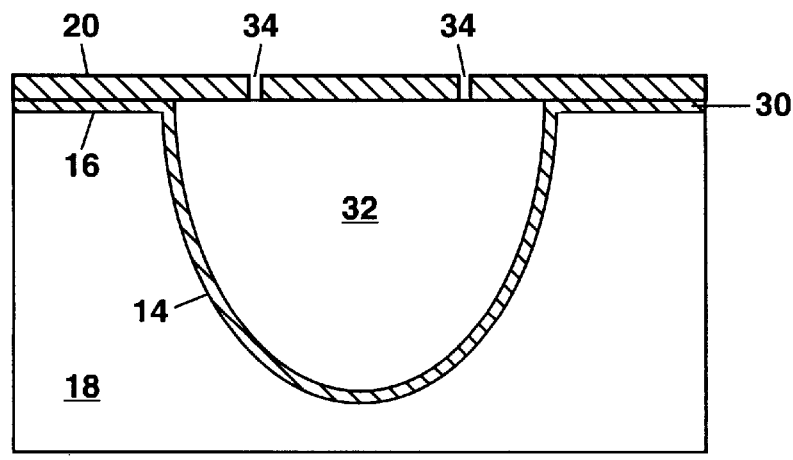

In FIG. 3f, one or more shaped openings 34 (e.g. circular, rectangular, square or slotted) with a width of up to a few microns can be formed through the silicon oxynitride covering layer 20 to expose the photoresist 32 for removal by solvent dissolution using, for example, acetone. These openings 34 can be formed by masking the covering layer 20 and etching (e.g. by reactive ion etching) down through the covering layer 20 to the photoresist 32. Alternately, the openings 34 can be formed by laser ablation.

Figure 3G:
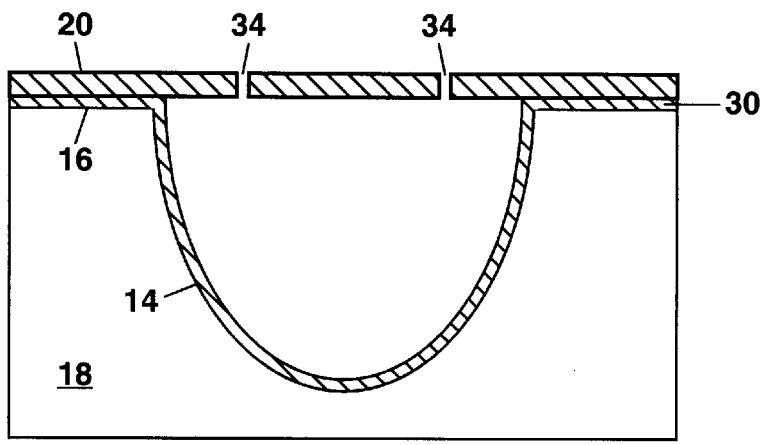

In FIG. 3g, the photoresist 32 can be removed from the trench 14 by immersing the substrate 18 into a solvent such as acetone, n-methyl pyrrolidone (NMP) or a commercial photoresist stripping solution for up to several hours with or without agitation or heating. If the sacrificial material 32 comprises a photodefinable polymer, then a suitable solvent can be used to remove the polymer from the trench 14 (e.g. NMP can be used to dissolve a photodefinable polyimide). Once the sacrificial material 32 has been removed from the trench 14, the silicon oxynitride layers 20 and 30 can optionally be densified by heating to a high temperature of 400° C. or more for about 30 seconds in a rapid thermal annealer.

Figure 3H:
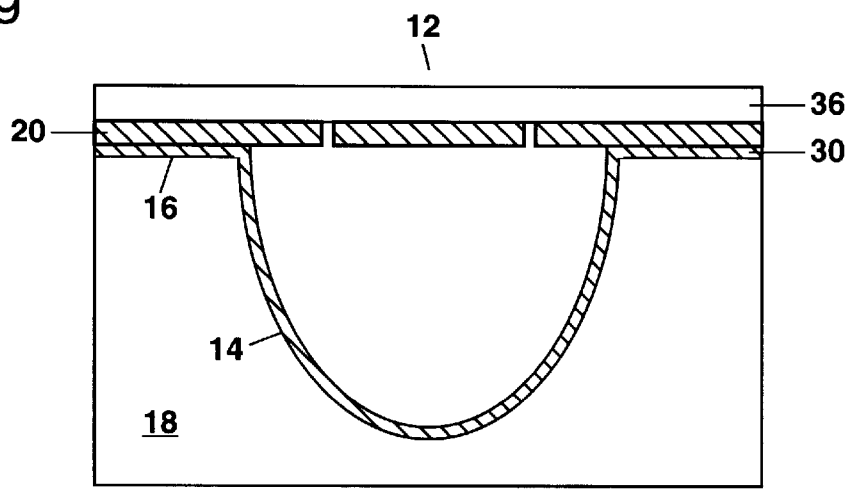

In FIG. 3h, the openings 34 can be sealed to complete formation of the hollow microchannel 12. This can be done by depositing an encapsulating layer 36 which can also strengthen the microchannel 12 for protection or to withstand a high internal fluid pressure. The encapsulating layer 36 can comprise, for example, a two-part elastomer (e.g. SYLGARD 184 manufactured by Dow Corning Incorporated), a photoactivated epoxy, a commercial potting compound, a polyimide or a spin-on glass. Alternately, the encapsulating layer 36 can comprise one or more metal or metal alloy layers that are deposited over the substrate by evaporation, sputtering, solution plating, or a combination thereof. The encapsulation layer 36 may or may penetrate down through the openings 34 in the covering layer 20.

A preferred process for forming an encapsulating layer 36 using a two-part elastomer is to mix the two-part elastomer in a 10:1 ratio and de-gas the two-part elastomer in a vacuum until bubbles no longer appear in the elastomer. The two-part elastomer can then be spun onto a glass cover slip which has first been cleaned by soaking in a 1:1:5 mixture of $NH_4OH:H_2O_2:H_2O$. The elastomer is initially spun onto the glass cover slip at 500 rpm for 45 seconds to distribute the elastomer. Then the speed of the spinner is increased to 2000 rpm for another 45 seconds to form a uniform thin coating of the elastomer on the glass cover slip. The glass cover slip and elastomer coating can then be contacted to the upper surface 16 of the substrate 18 covering the openings 34. The elastomer can be cured at either 90° C. for a few hours, or at room temperature for about 24 hours.

Figure 3I:
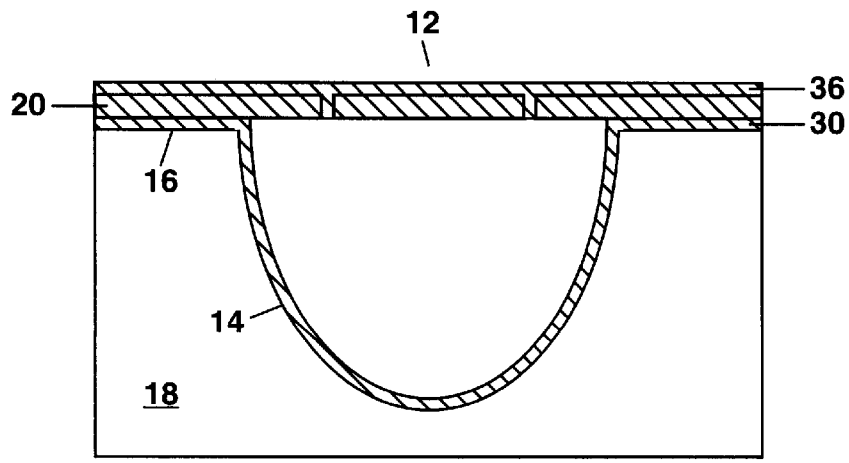

In some instances, the encapsulating layer 36 can comprise one or more additional silicon oxynitride layers deposited using a high-density plasma as described previously. The use of a silicon oxynitride encapsulating layer 36 can be advantageous for sealing the openings 34 through the covering layer 20 and for maintaining a uniform composition for the microchannel 12. The use of a silicon oxynitride encapsulating layer 36 is schematically illustrated in FIG. 3i. Additional encapsulating layers 36 comprising, for example, a two-part elastomer can be provided over the silicon oxynitride layer 20, if needed, for additional strength or protection.

Figure 4A:
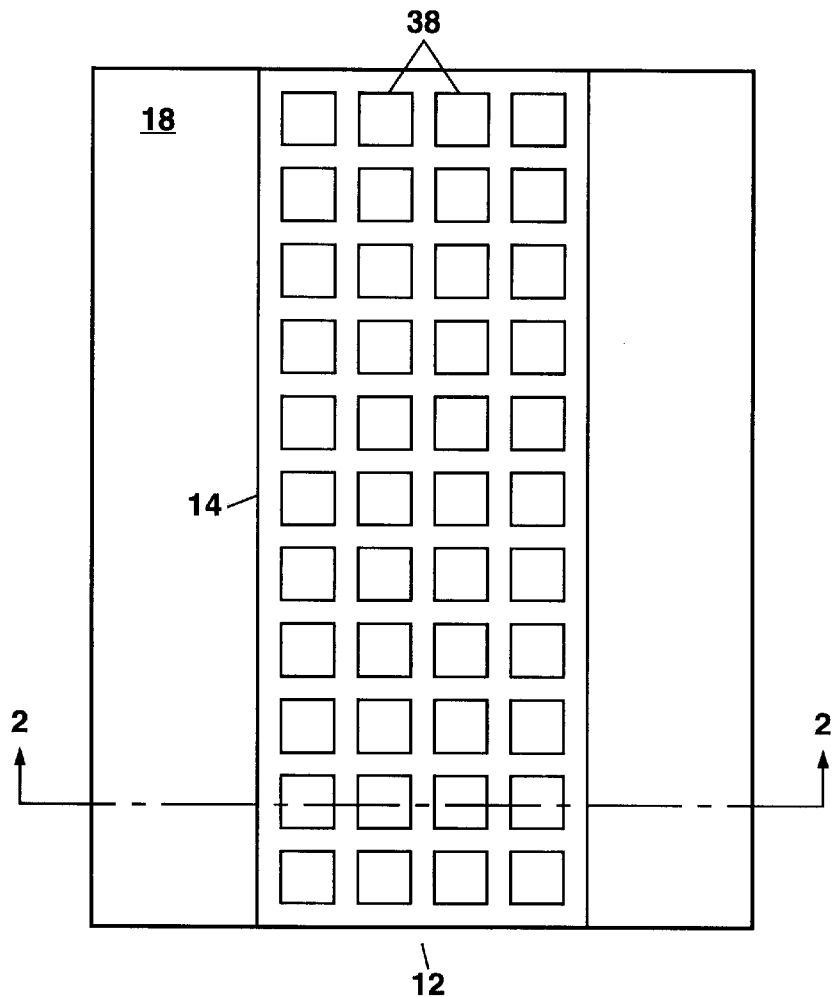
FIG. 4a shows a schematic partial plan view of another example of a fluid microchannel that can be formed below the surface of the substrate according to the present invention prior to depositing at least two silicon oxynitride layers for sealing the microchannel.
Figure 4B:
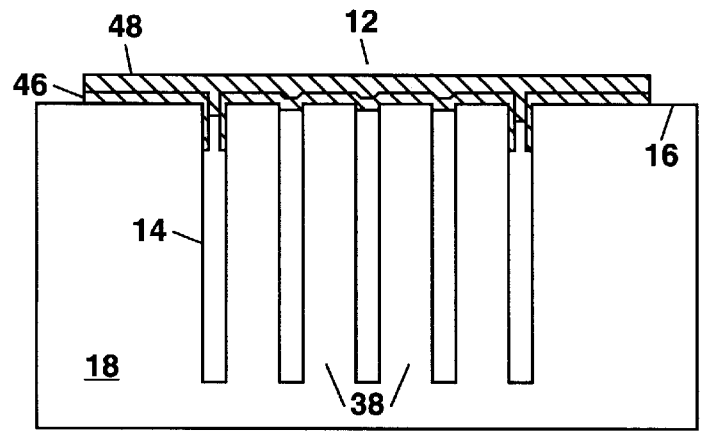
FIG. 4b shows a schematic cross-section view of the microchannel of FIG. 4a along the lines 2—2 including the silicon oxynitride layers.

FIG. 4a shows a schematic partial plan view of another type of fluid microchannel 12 that can be formed below the surface of a substrate 18 according to the present invention. The microchannel 12 is sealed with at least two deposited silicon oxynitride layers which are omitted from FIG. 4a for clarity. FIG. 4b shows a schematic cross-section view of the completed microchannel 12 of FIG. 4a along the lines 2—2 including the silicon oxynitride layers.

The microchannel 12 of FIGS. 4a and 4b includes a plurality of shaped columns 38 (also termed micro-posts) in the trench 14 arranged in an array for increasing a total surface area within the microchannel 12 (i.e. to form a packed microchannel 12). An increased surface area can be advantageous for chromatography or electrophoresis since the separation of different chemical species can be enhanced by increasing the surface area with which the chemical species interact while traversing the microchannel 12. This provides an increased stationary phase interaction which can reduce the length required for the microchannel 12. Chromatographic separation of different chemical species using electrokinetic pumping is described in further detail in an article by C. M. Matzke et al entitled "Quartz Channel Fabrication for Electrokinetically Driven Separations" published in the *Proceedings of the SPIE Conference on Microfluidic Devices and Systems,* SPIE Volume 3515, pages 164–171, September 1998, which is incorporated herein by reference.

FIGS. 5a–5h illustrate in schematic cross-section view a series of process steps that can be used to form the microchannel 12 of FIGS. 4a and 4b.

The various types of substrates 18 which can be used have been described previously. For electrokinetically driven separations, an electrically non-conductive substrate 18 is generally required; and a preferred material for this type of substrate 18 is Z-cut crystalline quartz which etches much faster in the Z-direction than in other directions. Crystalline quartz has a further advantage in that it is optically transparent over a wide range of wavelengths so that an optical detection system (e.g. a laser or light-emitting diode and a photodetector) can be integrated with the microchannel 12 to form an electrokinetic microchannel device 10. Therefore, the following discussion will describe formation of this embodiment of the microchannel 12 based on the use of a Z-cut crystalline quartz substrate 18. Those skilled in the art will understand that a microchannel 12 having a plurality of shaped columns 38 therein can be formed from other types of substrates which can be anisotropically etched, including silicon substrates. For example, a (110) silicon substrate can be preferentially etched with an etchant such as potassium hydroxide, with the etchant stopping on {111} planes which are oriented perpendicular to the upper surface of the substrate.

Figure 5A:
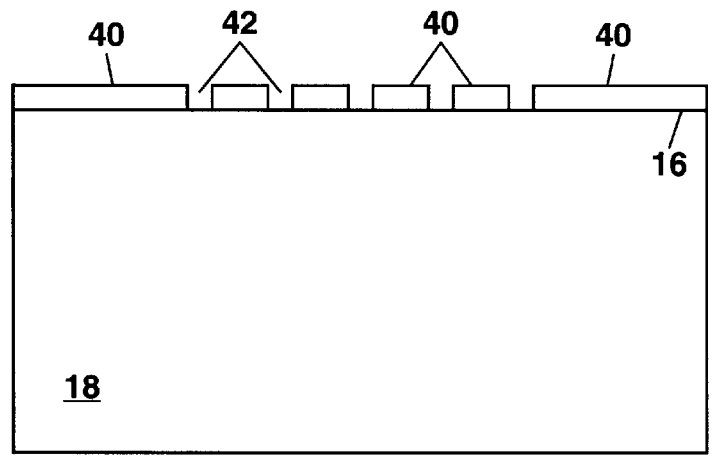
FIGS. 5a–5h illustrate a series of process steps that can be used to form the microchannel of FIGS. 4a and 4b.

In FIG. 5a, a photolithographically defined Cr/Au mask 40 is formed over the upper surface 16 of the crystalline quartz substrate 18 with a pattern 42 of openings which define the location of each microchannel 12 with the shaped columns 38 to be formed therein. To form a regular array of shaped columns 38 as shown in FIG. 4a, the mask 40 can be patterned to leave Cr/Au squares which define columns 38 to be formed with lateral dimensions of about 4–20 $\mu$m on a side and with a gap of about 3 $\mu$m between adjacent columns 38, and a 3-$\mu$m-spacing between the columns 38 and the sidewalls of the trench 14. This patterning of the Cr/Au mask 40 can be done by dry etching using argon ion milling through a photolithographically patterned photoresist mask (not shown).

Figure 5B:
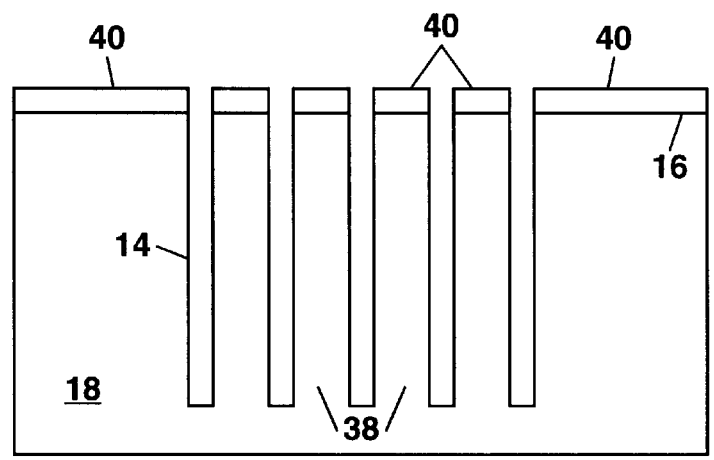

In FIG. 5b, the crystalline quartz substrate 18 can be anisotropically etched using 49% HF with no stirring. For a given spacing between the shaped columns 38, the measured etch depth increases as the width of each column 38 is reduced in size down to about 5 $\mu$m. Thus, etch rates appear to increase as the etchant becomes more diluted by etch reactants. An etch depth of about 40 $\mu$m can be achieved for eight hours of etching to produce a 5-cm-long serpentine microchannel 12 having a width of 80 $\mu$m, and packed with shaped columns 38 which are 5 $\mu$m on a side.

A change in shape of the columns 38 can also occur due to etching along crystalline planes so that Rrsx-facets appear due to fast etching in the Z-direction and slow etching along m-planes. This change in shape is especially pronounced as the width of the columns 38 is reduced so that the 5-$\mu$m-wide columns 38 appear substantially hexagonal in shape after etching. No substantial change in shape of the columns 38 or the gap between adjacent columns 38 occurs with increased etching depth (i.e. along the height of the columns 38) so that after etching the shaped columns 38 and sidewalls of the trench 14 are aligned substantially perpendicular to the upper surface 16 of the substrate as shown in FIG. 5b.

Two-sided processing of the crystalline quartz substrate 18 can be performed to fabricate one or more packed microchannels 12 below the upper surface 16 of the substrate 18 and to form open microchannels 12 without any columns 38 on a lower surface of the substrate 18. The two types of microchannels 12 can be interconnected with via-holes formed through the substrate 18. The open microchannels 12 can then be connected to macrotubing tubing 24 to form sample injection and output ports.

A Cr/Au mask is used on the lower surface of the substrate 18 to define the open microchannels 12, with the Cr/Au mask being patterned by a photoresist mask, followed by etching of the Cr/Au mask using KI/I$_2$ and chromium etchants. When two-sided processing of the crystalline quartz substrate 18 is used, one side can be protected during etching of the other side by a covering of a mylar sheeting or an unpatterned layer of photoresist. Once etching is complete, the Cr/Au masks can be removed from each side of the substrate 18 using the KI/I$_2$ and chromium etchants.

Figure 5C:
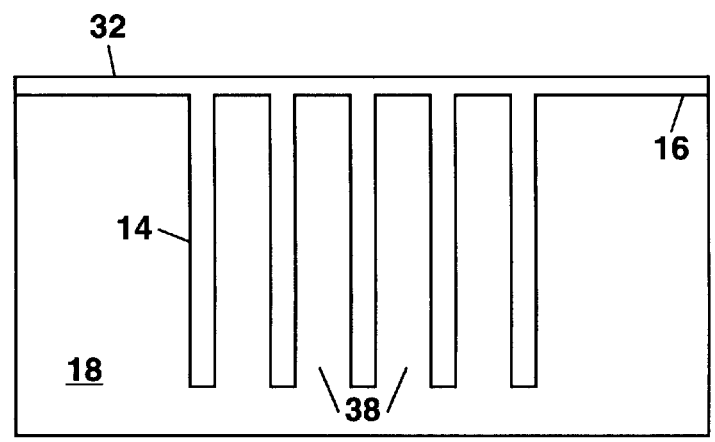

In FIG. 5c, a sacrificial material 32 preferably comprising photoresist can be spun on over the crystalline quartz substrate 18 to fill in the etched areas therein. The photoresist 32 can be, for example, a positive-tone thick resist which can be spun on for a short time to minimize flow of the photoresist out of the etched trench 14.

Figure 5D:
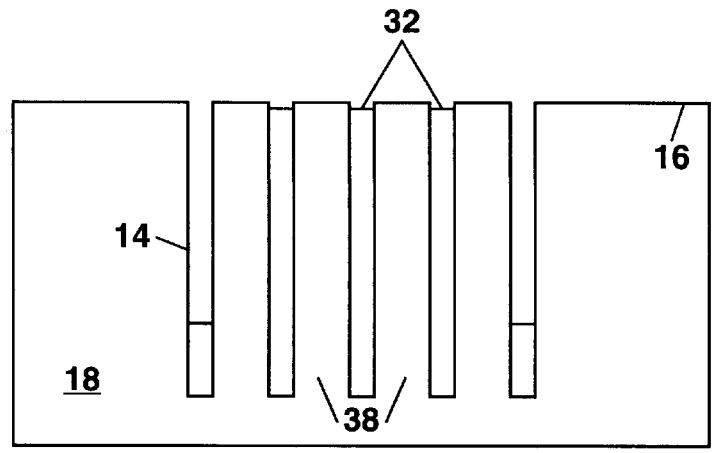

In FIG. 5d, the photoresist 32 outside the trench 14 and inside the trench 14 near the sidewalls is photolithographically exposed and developed to remove this portion of the photoresist 32. A double exposure (e.g. 8 seconds) can be used to expose the photoresist 32 to be removed within the trench 14 which can be, for example, up to 40–50 $\mu$m thick. An over-develop time of one minute can be used to aid in removal of the photoresist 32 from within the trench 14, and also from the tops of the shaped columns 38 in a central portion of the trench 14. The removal of the photoresist 32 near the sidewalls of the trench 14 need not be complete, but need only be removed to an extent that will allow the formation of open windows 44 in this region so that the remaining photoresist 32 can be removed by solvent dissolution.

After removal of the photoresist 32 as described above, an oxygen plasma "de-scum" step can be used to clear any photoresist residue from the tops of the shaped columns 38, and from the upper surface 16 of the substrate 18 thereby improving adhesion of a subsequently-deposited silicon oxynitride covering layer (i.e. a first layer 46 as described hereinafter). This can result in the photoresist 32 between the shaped columns 38 being slightly recessed below the upper surface 16 of the substrate as shown in FIG. 5d.

Figure 5E:
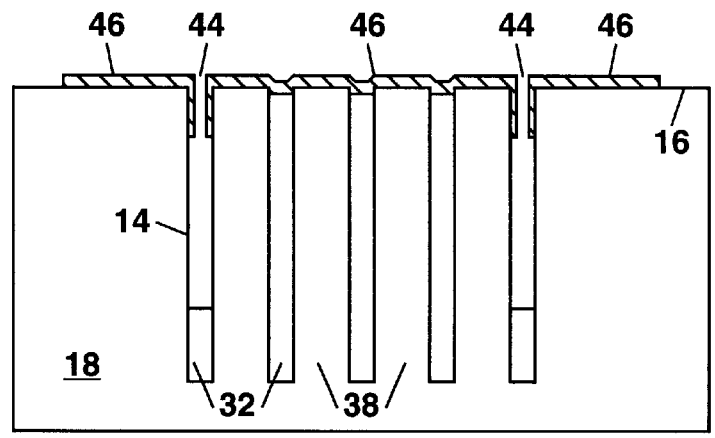
Figure 5F:
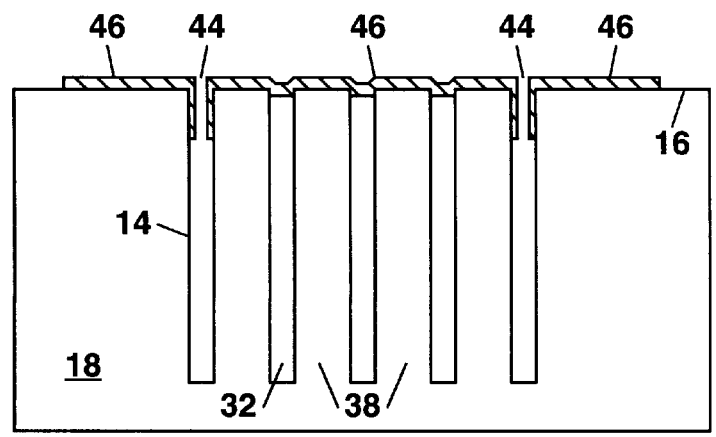

In FIG. 5e, a first layer 46 of silicon oxynitride can be deposited over a portion of the substrate and patterned to leave the windows 44 to provide access to the trench 14. The first layer 46 of silicon oxynitride and subsequent silicon oxynitride layers can be deposited using a high-density plasma (e.g. an ECR plasma) as described previously. For example, the thickness of the first layer 46 of silicon oxynitride can be about 350 nanometers using a 30 minute ECR deposition. At this thickness, the first layer 46 of silicon oxynitride only partially fills in the windows 44 leaving room for entry of a solvent (e.g. acetone) to dissolve away the remaining photoresist 32 as shown in FIG. 5f. The solvent dissolution step can proceed for several hours (e.g. 3–5 hours) as described previously.

Figure 5G:
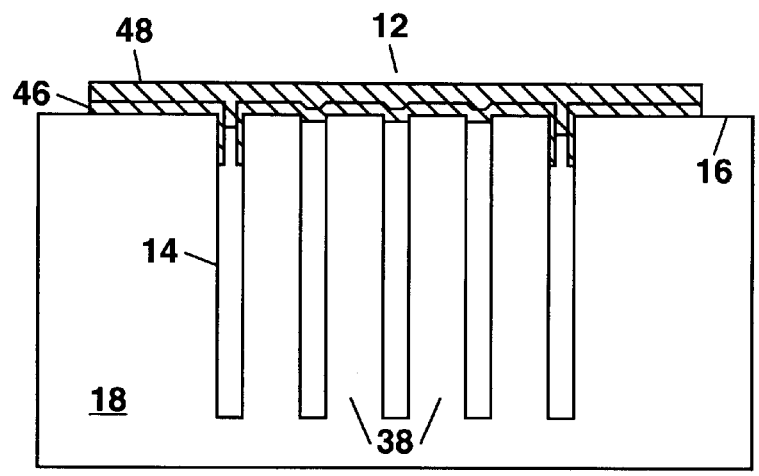

In FIG. 5g, a second layer 48 of silicon oxynitride can be deposited over the substrate to fill in the windows 44. This second layer 48 of silicon oxynitride can be, for example, about 1.2 $\mu$m thick and can be deposited from the high-density plasma at a rate of about 60 nanometers/minute. Additional layers of silicon oxynitride can be deposited, if needed, to completely fill in the windows 44 to form a hollow microchannel 12. An annealing step can optionally be provided to densify the silicon oxynitride layers 46 and 48 after removal of the photoresist sacrificial material 32.

Figure 5H:
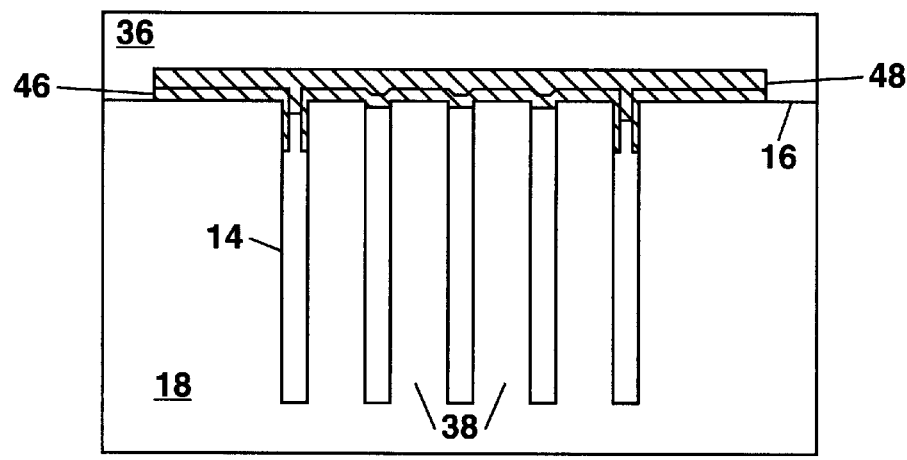

In FIG. 5h, an encapsulating layer 36 as described previously (e.g. comprising a two-part elastomer, an epoxy, a commercial potting compound, a polyimide, or a spin-on glass) can also be provided over the microchannel 12 if needed for protection or for strengthening the microchannel 12 to withstand higher internal fluid pressures. In some embodiments of the present invention, the encapsulating layer 36 can be substituted for the second layer 48 of silicon oxynitride to simplify processing and reduce manufacturing cost.

Figure 6A:
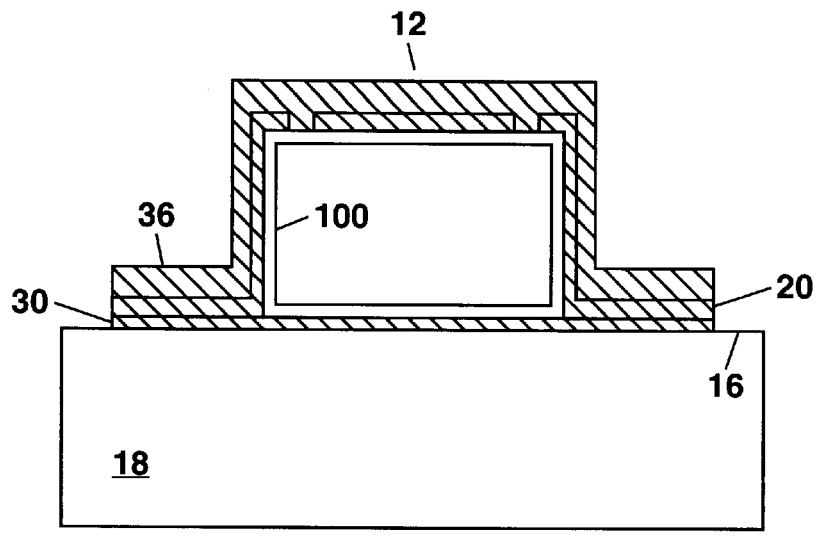
FIGS. 6a and 6b show schematic cross-section views of two examples of fluid microchannels that can be formed above the upper surface of the substrate according to the present invention.

After formation, the microchannel 12 can be coated inside with a stationary phase coating material 100 as used in the art of chromatography or electrophoresis (see FIG. 6a). Commonly used stationary phase coating materials 100 consist of polymers synthesized with specific chemical groups with the proper physico-chemical interactions to cause separation of a chemical species of interest from a gaseous or liquid sample to be analyzed. Different methods can be used to coat the microchannel 12 of FIGS. 4a and 4b with a particular stationary phase coating material 100. For example, this can be done by pushing a plug of a selected stationary phase coating material 100 (e.g. a long-chain hydrocarbon based on silane chemistry) through the microchannel 12 using pressurized gas. Alternately, the microchannel 12 can be filled with the stationary phase coating material 100; and then the excess material 100 can be removed from the microchannel 12 by applying a vacuum at one end of the microchannel 12 (e.g. via macrotubing 24).

Electrodes can be formed spaced along the microchannel 12 for electrokinetic pumping. This can be done by forming openings to the interior of the microchannel 12 and depositing a chemically-resistant metal (e.g. platinum or gold) to form the electrodes. Alternately, the electrodes can be formed by depositing metal at within the microchannel 12 prior to deposition of the silicon oxynitride layers 46 and 48. In some cases, the electrodes can be formed in fluid reservoirs connected to the microchannel 12.

Figure 6B:
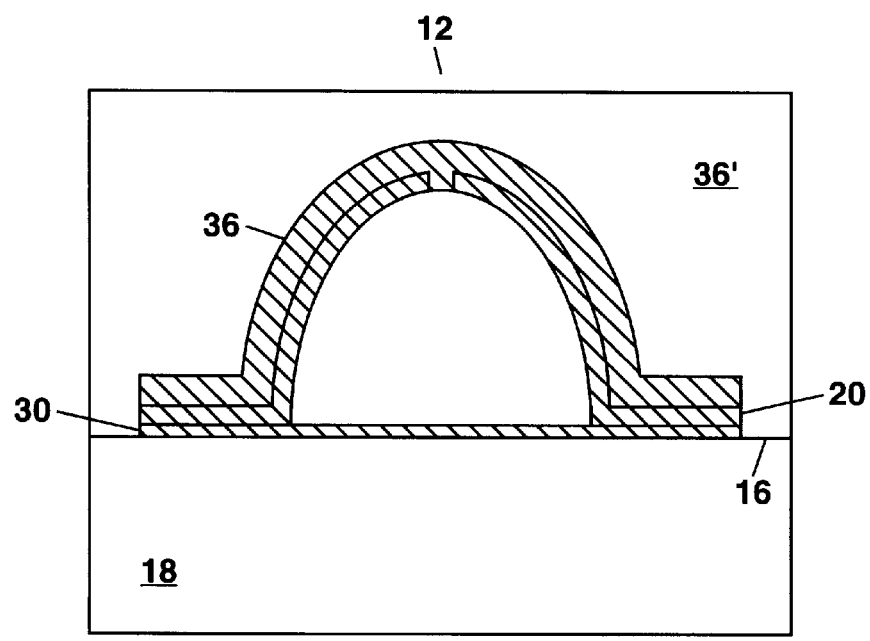

According to the present invention, one or more microchannels 12 can also be formed above an upper surface 16 of a substrate 18 (i.e. to form above-surface microchannels 12). FIGS. 6a and 6b illustrate in cross-section view examples of microchannels 12 that can be formed above a substrate 18 according to the present invention. FIG. 6a shows an example of a microchannel 12 formed above the substrate 18 with a rectangular or square cross-section; and FIG. 6b shows an example of a curved microchannel 12. The formation of these types of microchannels 12 can be understood with reference to FIGS. 7a–7.

Figure 7A:
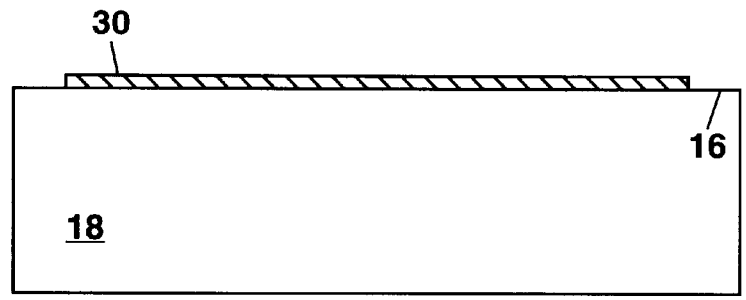
FIGS. 7a–7i illustrate a series of process steps that can be used to form the microchannels of FIGS. 6a and 6b.

In FIG. 7a, a substrate 18 can be initially prepared for formation of the microchannel 12 by depositing a silicon oxynitride underlayer 30 on a portion of the upper surface 16 of the substrate 18. The substrate 18 can comprise any of the materials described previously, including semiconductors, crystalline quartz, fused silica, glasses, ceramics, polymers, metals and ferroelectrics.

In FIG. 7a, the underlayer 30, which has a composition in the range previously described and a layer thickness from 0.05 $\mu$m to 3 $\mu$m, allows formation of the microchannel 12 that is completely lined with silicon oxynitride to present a uniform composition surface for fluid flow, thereby eliminating possible detrimental effects due to contact of the fluid with surfaces of different compositions, or to prevent a chemical reaction with the substrate 18. Deposition of the silicon oxynitride underlayer 30 can be performed using a high-density plasma as described previously. The underlayer 30 can also serve to electrically insulate the microchannel 12 and fluid therein from an electrically-conducting substrate 18 (e.g. for electrokinetic pumping of the fluid). In some embodiments of the present invention, the process step of FIG. 7a can be omitted when it is not essential to have a uniform-composition microchannel 12.

Figure 7B:
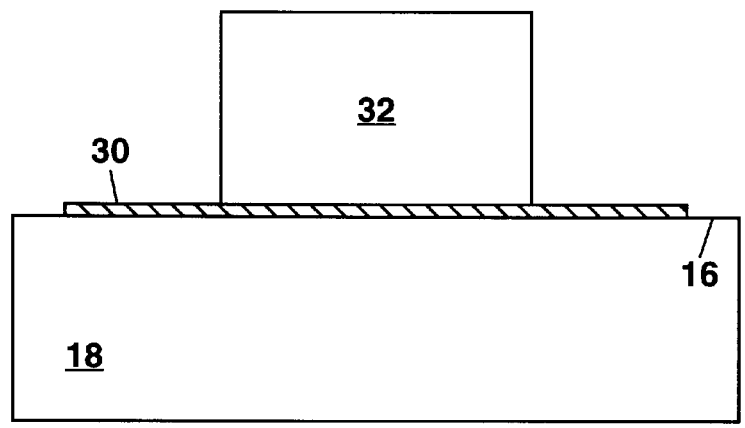

In FIG. 7b, one or more layers of a sacrificial material 32 are deposited over the substrate 18 and are photolithographically patterned to leave an elongate-shaped mold for defining the dimensions of the microchannel 12 being formed. The sacrificial material 32 preferably comprises photoresist. After forming the mold as shown in FIG. 7b, an oxygen plasma "de-scum" step can be used as described previously to remove any photoresist residue from exposed portions of the silicon oxynitride underlayer 30 not covered by the mold. The oxygen plasma "de-scum" step can be limited in time duration to prevent substantial erosion of the photoresist 32 which forms the mold.

Figure 7C:
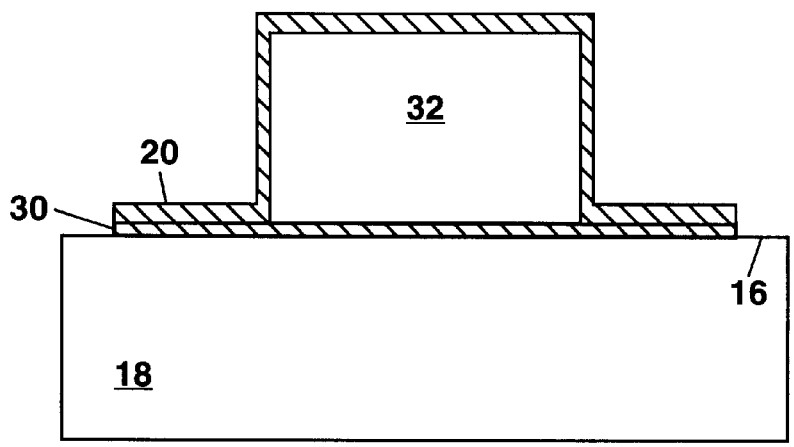

In FIG. 7c, a silicon oxynitride covering layer 20 is deposited over the mold (i.e. over the photoresist 32) and over the exposed portions of the underlayer 30 using the high-density plasma. During this step, the substrate 18 is maintained at a temperature of $\leq 100°$ C. and preferably near room temperature (e.g. 20–30° C.). The thickness of the covering layer 20 can be in the range of 0.5–10 $\mu$m and preferably about 2 $\mu$m, with a composition similar to that of the underlayer 30.

Figure 7D:
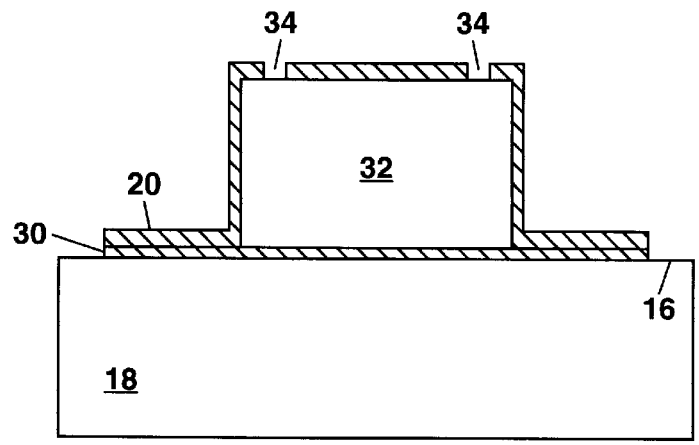

In FIG. 7d, one or more openings 34 can be formed through the covering layer 20 to expose the photoresist 32 for removal by solvent dissolution. The openings 34, which can have an arbitrary shape (e.g. a plurality of micron-sized holes, or one or more slots), can be formed by etching (e.g. reactive ion etching) using a photolithographically defined mask, or alternatively by laser ablation. In some instances, the photoresist 32 can be removed through an open end of the microchannel 12, even though the microchannel 12 can have a length of many centimeters. For example, removal of the photoresist 32 from the open ends of a serpentine microchannel that is 28-centimeters long, 80-$\mu$m wide and 30-$\mu$m high can be accomplished in a reasonable time of 2–3 hours.

Removal of the photoresist 32 by solvent dissolution can also be performed through one or more via-holes 22 formed through the substrate 18 and connected with the microchannel 12 (see FIG. 1b). Such via-holes 22 through the substrate 18 (e.g. a silicon substrate) can be formed, for example, by using a deep reactive ion etching process which combines multiple anisotropic etching steps with steps for simultaneously depositing an isotropic polymer / inhibitor to minimize lateral etching as disclosed in U.S. Pat. No. 5,501,893 to Laermer et al. In some cases, it will be preferable to form the via-holes 22 prior to forming the microchannel 12. If this is done, a photoresist 32 can be selected with an appropriate viscosity which will allow the photoresist 32 to cover the via-holes 22 during formation of the microchannel 12.

Figure 7E:
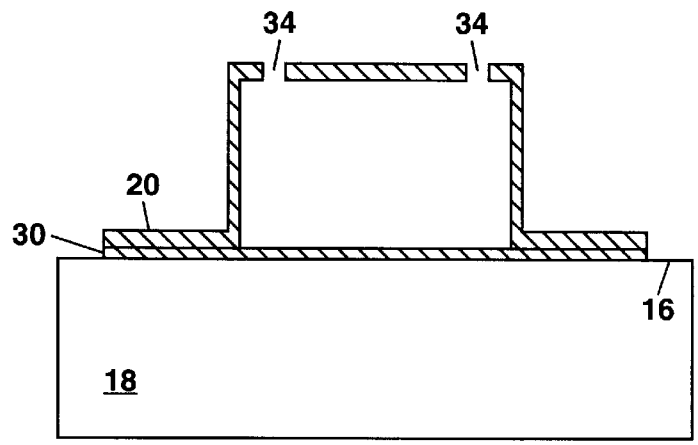

In FIG. 7e, the photoresist 32 is removed from the microchannel 12 being formed by placing the substrate 18 in a solvent bath (e.g. acetone) with or without agitation and/or heating. The solvent enters the microchannel 12 through the openings 34 and dissolves away the photoresist 32. This process can take several hours.

Figure 7F:
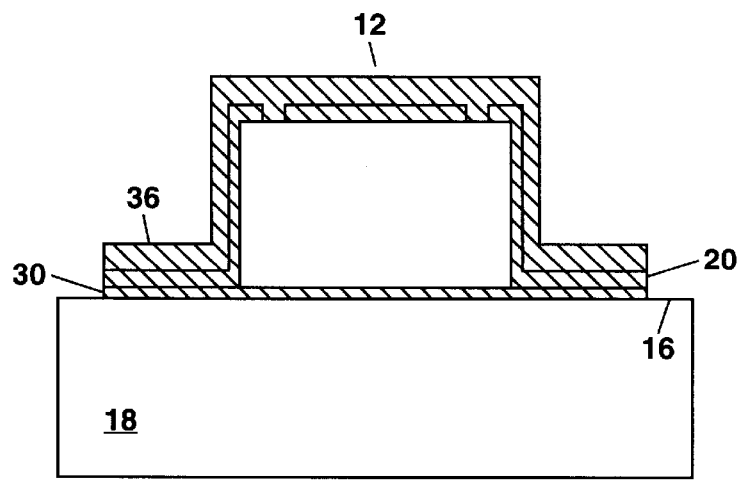

In FIG. 7f, the openings 34 can be sealed with an encapsulating layer 36 as described previously with reference to FIGS. 3h and 3i. To form a microchannel 12 that is completely lined with silicon oxynitride, the encapsulating layer 36 can comprise another layer of silicon oxynitride deposited using the high-density plasma as described previously. This silicon oxynitride encapsulating layer 36 preferably has a composition that is substantially the same as the layers 20 and 30, and has a layer thickness which is generally in the range of 0.5–10 $\mu$m. The exact thickness of the silicon oxynitride encapsulating layer 36 will depend on the size of the openings 34 to be sealed, and also on the strength needed for the microchannel 12.

This completes formation of the microchannel 12. For chromatographic applications, the interior of the microchannel 12 can be coated with a stationary phase coating material 100 as shown in FIG. 6a and as previously described with reference to FIG. 5h.

To form a curved microchannel 12 above the upper surface 16 of the substrate 18, the steps described hereinafter with reference to FIGS. 7g–7i can be performed after the steps of FIGS. 7a and 7b.

Figure 7G:
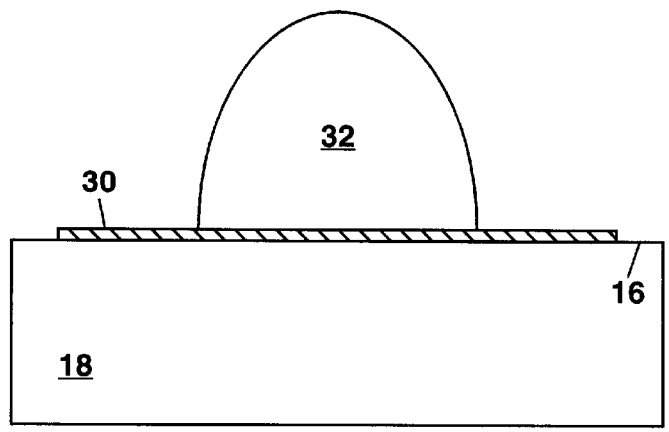
Figure 7H:
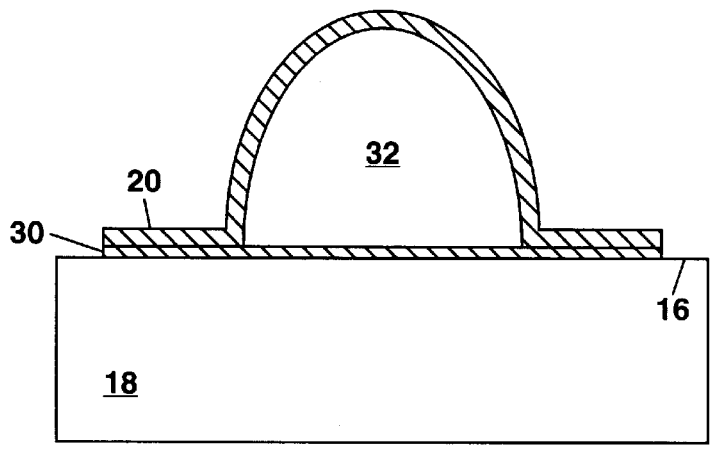

In FIG. 7g, the photoresist 32 which forms the mold for the microchannel 12 to be formed can be heated to above a reflow temperature (i.e. to a temperature generally in the range of 80–140° C., and preferably about 130° C.) for sufficient time (i.e. from a few seconds to about 20 seconds) so that surface tension will cause the photoresist 32 to flow, thereby rounding the exposed sides and edges of the photoresist 32 to form a curved mold. The exact cross-section shape of the curved mold (e.g. semi-circular or semi-elliptical) will depend on the width and height of the photoresist 32 and the temperature used to soften or flow the photoresist 32.

Figure 7I:
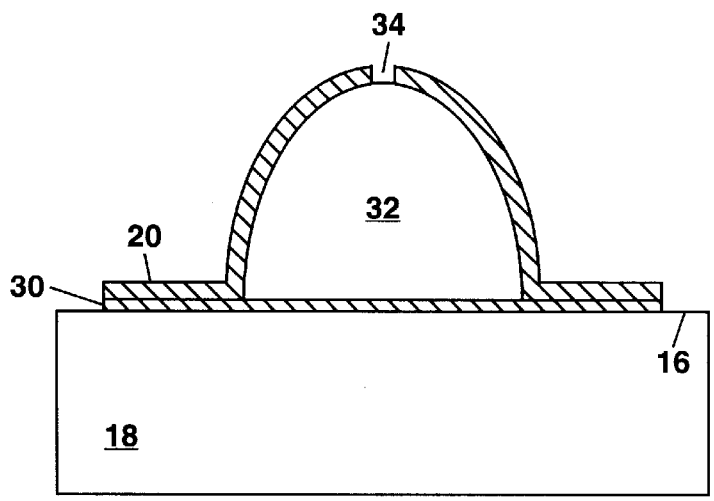
Figure 7J:
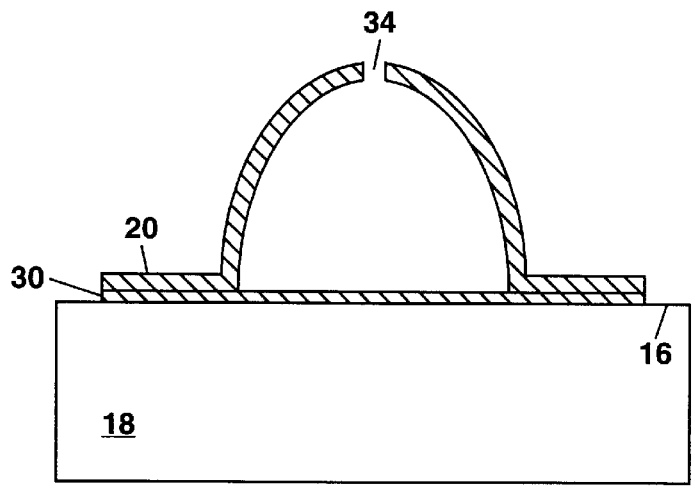
Figure 7K:
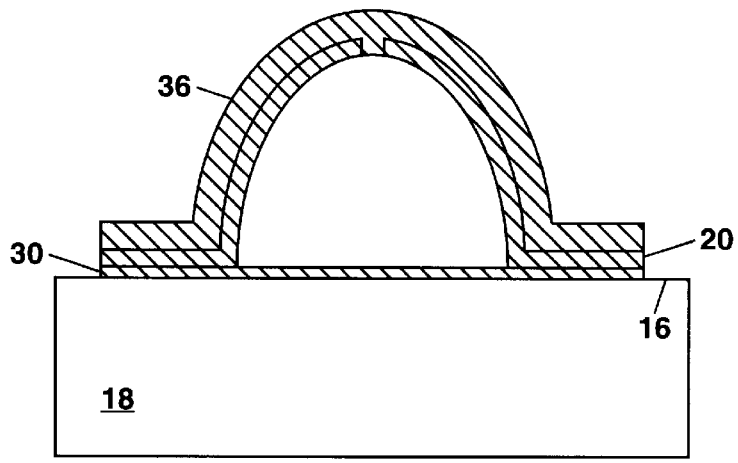
Figure 7L:
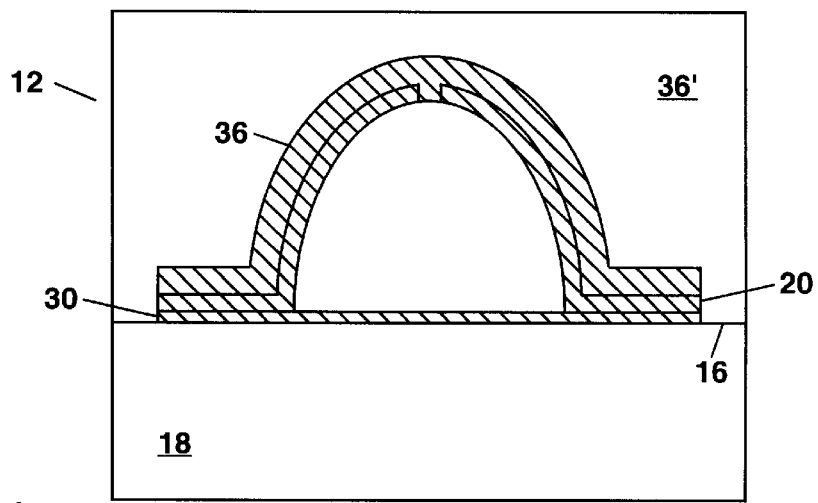

Further processing to form the curved microchannel 12 as shown in FIGS. 7h–7k can proceed as described with reference to FIGS. 7c–7f. In FIG. 7i, an optional second encapsulating layer 36' can be provided for local or global substrate planarization or to further increase the strength of the curved microchannel 12. The second encapsulating layer 36' can comprise a two-part elastomer, an epoxy, a potting compound, a polyimide, a spin-on glass or the like. If a thermal annealing step is used to densify the various silicon oxynitride layers, this step is preferably performed before application of the second encapsulating layer 36'.

The types of above-surface microchannels 12 shown in FIGS. 6a and 6b can be combined with the sub-surface microchannels 12 of FIGS. 2a and 2b or FIGS. 4a and 4b to form a microchannel device 10 with multiple interconnecting or crossing microchannels (i.e. a network of microchannels 12). Furthermore, additional levels of microchannels 12 can be formed with or without planarizing each underlying level of microchannels 12 (e.g. by an encapsulating layer 36' as shown in FIG. 7i).

Figure 8:
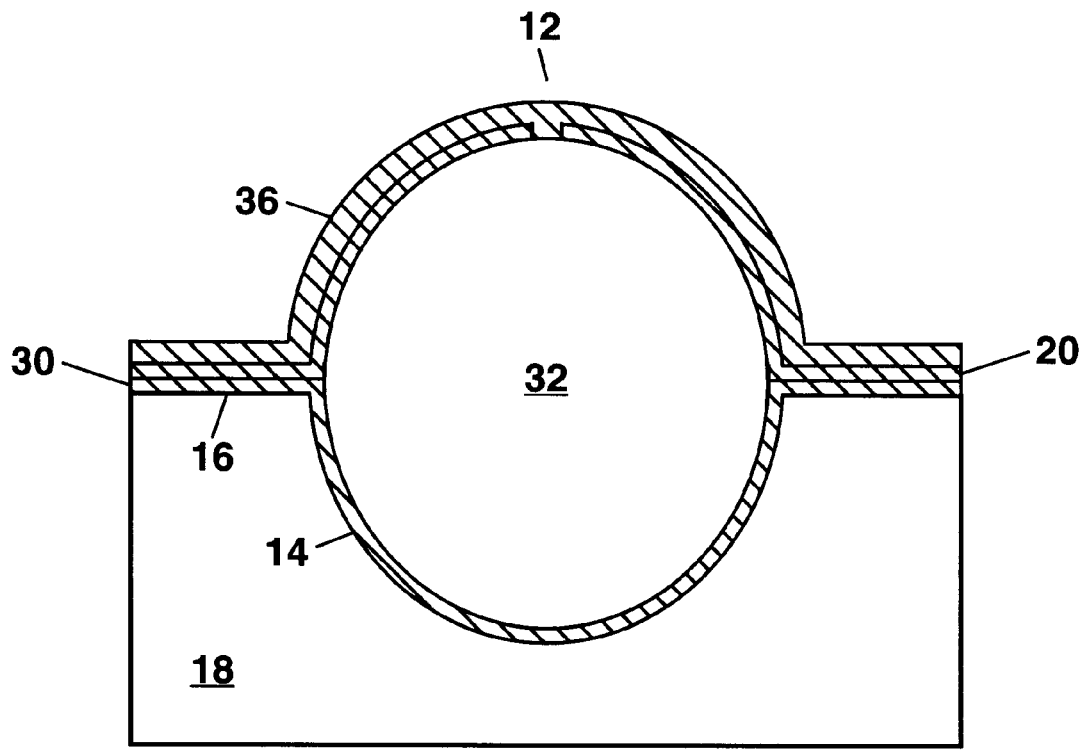
FIG. 8 shows a schematic cross-section view of an example of a fluid microchannel that can be formed which extends both above and below the surface of the substrate.

The teachings of the present invention for forming above-surface and sub-surface microchannels 12 can also be combined as shown in FIG. 8 to form a microchannel 12 which lies partially below the upper surface 16 of the substrate 18, and partially above the surface 16. FIGS. 9a–9f schematically illustrate the formation of a microchannel 12 having a curved cross-section shape (e.g. circular or elliptical) by combining some of the process steps used to form the curved sub-surface microchannel 12 of FIG. 2b with additional process steps used to form the curved above-surface microchannel 12 of FIG. 6b.

Figure 9A:
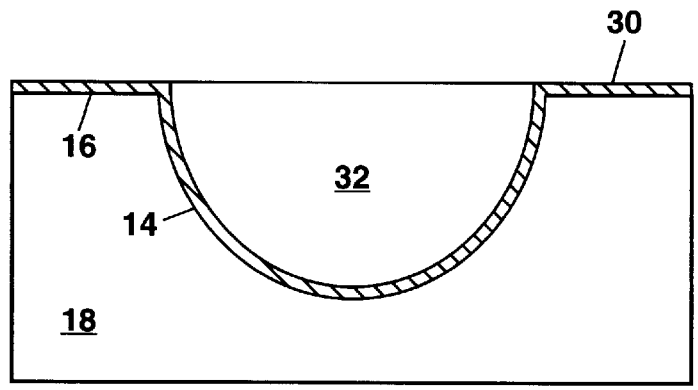
FIGS. 9a–9c illustrate formation of the microchannel of FIG. 8.

In FIG. 9a, a trench 14 is lined with a silicon oxynitride underlayer 30 and then filled with photoresist 32 as previously described with reference to FIGS. 3a–3d.

Figure 9B:
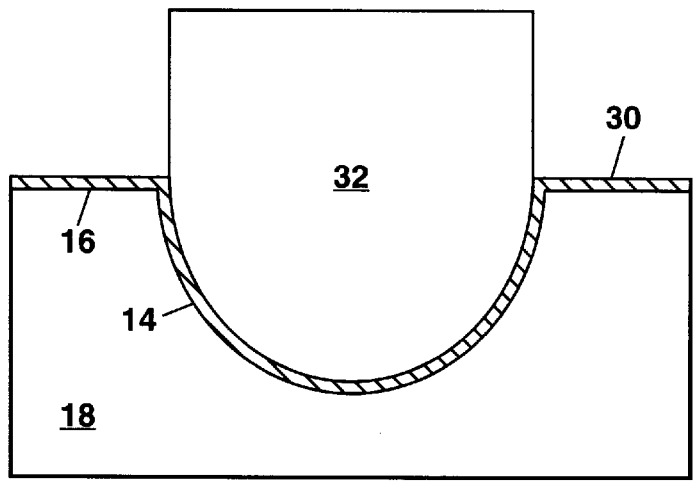

In FIG. 9b, one or more additional layers of photoresist 32 are spun on over the substrate 18 and patterned as shown to form an elongate-shaped mold extending upward from the upper surface 16 of the substrate 18 as described with reference to FIG. 7b.

Figure 9C:
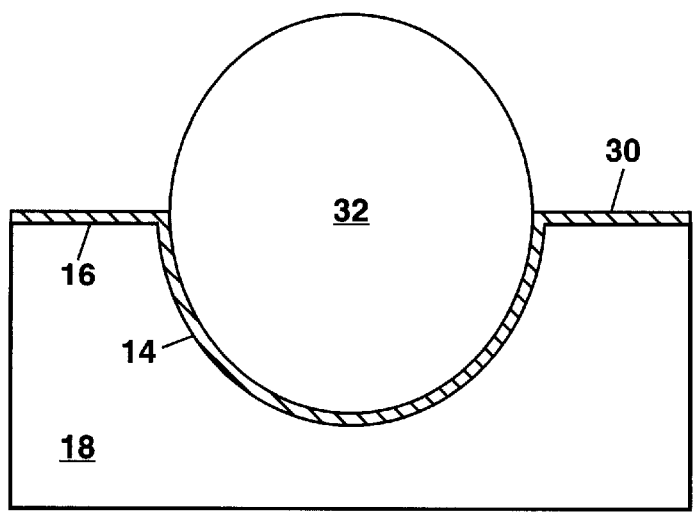

In FIG. 9c, the substrate 18 is heated to flow the photoresist 32 as described with reference to FIG. 7g, thereby rounding the portion of the photoresist 32 extending upward beyond the upper surface 16 of the substrate 18. Further processing can then proceed to form the microchannel 12 with a curved cross-section shape following the process steps outlined with reference to FIGS. 7h–7k.

The process described herein for fabricating one or more microchannels 12 on a substrate 18 is compatible with standard integrated circuit processing so that integrated circuitry can be formed on the upper surface 16 of the substrate 18 prior to the formation of the microchannels 12. This allows the formation of electrodes which can penetrate into the microchannels 12 or reservoirs connected thereto for electrokinetic pumping of fluids. Additionally, electronic circuitry can be fabricated on the substrate 12 to process analytical signals derived using one or more microchannels 12, or to control operation of a microchannel device 10.

The microchannels 12 formed according to the present invention also have non-analytical applications. For example, one or more microchannels 12 can be formed on a front side or on a backside of an integrated circuit for localized or global substrate cooling. Localized front-side cooling of critical heat-producing circuit elements (e.g. power or output transistors) can be achieved by forming one or more microchannels 12 above or proximate to the heat-producing elements to cool the elements via a circulating fluid coolant.

The matter set forth in the foregoing description and accompanying drawings is offered by way of illustration only and not as a limitation. Other applications and variations of the present invention will become evident to those skilled in the art. The actual scope of the invention is intended to be defined in the following claims when viewed in their proper perspective based on the prior art.

What is claimed is:

1. A method for forming a fluid microchannel in a substrate, comprising steps for:
   (a) forming a trench below an upper surface of the substrate;
   (b) filling the trench with a sacrificial material;
   (c) forming at least one silicon oxynitride layer covering the trench; and
   (d) removing the sacrificial material from the trench, thereby forming the microchannel.

2. The method of claim 1 wherein the step for forming the trench comprises forming the trench by etching.

3. The method of claim 2 wherein the step for forming the trench comprises etching the trench in a substrate selected from the group consisting of semiconductors, crystalline quartz, fused silica, glasses, ceramics, polymers, metals, and ferroelectrics.

4. The method of claim 1 wherein the step for forming the trench comprises forming the trench with a pair of sidewalls aligned substantially perpendicular to the upper surface of the substrate.

5. The method of claim 4 wherein the step for forming the trench further comprises forming a plurality of shaped columns in the trench, with the shaped columns being aligned substantially perpendicular to the upper surface of the substrate.

6. The method of claim 1 wherein the step for forming the trench comprises forming the trench with curved sidewalls.

7. The method of claim 1 wherein the step for filling the trench with the sacrificial material comprises spinning on a photoresist or photodefinable polymer over the surface of the substrate and in the trench, photolithographically exposing and developing the photoresist or photodefinable polymer to remove a portion thereof outside of the trench.

8. The method of claim 7 wherein the step for removing the sacrificial material comprises removing the photoresist or photodefinable polymer from the trench by dissolution using a solvent.

9. The method of claim 1 further including a step for cleaning the substrate to remove any sacrificial material from the upper surface of the substrate after the step for filling the trench with the sacrificial material.

10. The method of claim 9 wherein the step for cleaning the substrate comprises exposing the substrate to an oxygen plasma for sufficient time to remove the sacrificial material from the upper surface of the substrate.

11. The method of claim 1 wherein the step for depositing the silicon oxynitride layer comprises depositing the silicon oxynitride layer by a high-density plasma deposition process.

12. The method of claim 11 wherein the step for depositing the silicon oxynitride layer is carried on at a substrate temperature of $\leq 100°$ C.

13. The method of claim 11 wherein the high-density plasma deposition process comprises electron-cyclotron resonance (ECR) plasma deposition or inductively-coupled plasma (ICP) deposition.

14. The method of claim 13 wherein the silicon oxynitride after deposition thereof has a composition $Si_wO_xN_yH_z$, with 25–65 atomic percent (at. %) silicon (Si), 5–40 at. % oxygen (O), 10–40 at. % nitrogen (N), and 0–25 at. % hydrogen (H).

15. The method of claim 14 further including a step for densifying the silicon oxynitride by thermal annealing after the step for removing the sacrificial material from the trench.

16. The method of claim 1 further including a step for lining the trench with an underlayer of silicon oxynitride prior to the step for filling the trench with the sacrificial material.

17. The method of claim 16 wherein the underlayer has a thickness in the range of 0.05 microns.

18. The method of claim 1 wherein the step for removing the sacrificial material from the trench comprises forming at least one opening through the silicon oxynitride layer to expose the sacrificial material.

19. The method of claim 18 further including a step for sealing each opening through the silicon oxynitride layer after the step for removing the sacrificial material from the trench.

20. The method of claim 1 further including a step for depositing an encapsulating layer over the silicon oxynitride layer after the step for removing the sacrificial material.

21. A method for forming a fluid microchannel on a substrate, comprising steps for:
(a) depositing a sacrificial material over an upper surface of the substrate and patterning the sacrificial material to form an elongate-shaped mold for the microchannel to be formed on the substrate;
(b) depositing at least one covering layer of silicon oxynitride over the patterned sacrificial material, and providing at least one opening for exposing the sacrificial material; and
(c) removing the sacrificial material through the opening, thereby forming the microchannel.

22. The method of claim 21 wherein the substrate comprises a material selected from the group consisting of semiconductors, crystalline quartz, fused silica, glasses, ceramics, polymers, metals, and ferroelectrics.

23. The method of claim 21 wherein the step for depositing the sacrificial material comprises spinning on a photoresist over the upper surface of the substrate, and patterning the photoresist to form the mold.

24. The method of claim 23 further including a step for heating the patterned photoresist and flowing the patterned photoresist, thereby producing a curved cross-section shape for the mold.

25. The method of claim 23 wherein the step for removing the sacrificial material comprises removing the photoresist by solvent dissolution.

26. The method of claim 23 further including a step for cleaning the upper surface of the substrate to remove any photoresist residue after patterning of the photoresist by exposing the upper surface of the substrate to an oxygen plasma for sufficient time to remove the photoresist residue.

27. The method of claim 21 wherein the step for depositing the covering layer comprises depositing the covering layer by a high-density plasma deposition process.

28. The method of claim 27 wherein the high-density plasma deposition process is carried on at a substrate temperature of $\leq 100°$ C.

29. The method of claim 27 wherein the high-density plasma deposition process comprises electron-cyclotron resonance (ECR) plasma deposition or inductively-coupled plasma (ICP) deposition.

30. The method of claim 21 wherein the silicon oxynitride covering layer after deposition thereof has a composition $Si_wO_xN_yH_z$, with 25–65 atomic percent (at. %) silicon (Si), 5–40 at. % oxygen (O), 10–40 at. % nitrogen (N), and 0–25 at. % hydrogen (H).

31. The method of claim 30 further including a step for densifying the silicon oxynitride covering layer by thermal annealing after the step for removing the sacrificial material.

32. The method of claim 21 further including a step for lining the upper surface of the substrate with an underlayer of silicon oxynitride layer prior to the step for depositing the sacrificial material.

33. The method of claim 32 further including a step for treating an exposed portion of the underlayer prior to the step for depositing the covering layer to improve adhesion of the covering layer to the exposed portion of the underlayer.

34. The method of claim 21 further including a step for forming a trench in the substrate prior to the step for depositing the sacrificial material.

35. The method of claim 34 further including a step for lining the trench with an underlayer of silicon oxynitride layer prior to the step for depositing the sacrificial material.

36. The method of claim 34 wherein the step for depositing the sacrificial material over the substrate fills the trench, with the sacrificial material extending upward beyond the upper surface of the substrate.

37. The method of claim 35 wherein the mold formed by patterning the sacrificial material lies within the trench and further extends upward beyond the upper surface of the substrate.

38. The method of claim 36 wherein the sacrificial material comprises a photoresist, and further including a step, after patterning of the photoresist to form the mold, for heating the photoresist to a temperature sufficiently high to produce a flowing of the photoresist, thereby generating a curved cross-section shape for the mold.

39. The method of claim 21 further including a step for sealing each opening after the step for removing the sacrificial material.

40. The method of claim 21 further including a step for depositing an encapsulating layer over the covering layer after the step for removing the sacrificial material.

* * * * *